(12) United States Patent
Stone et al.

(10) Patent No.: US 8,057,729 B2
(45) Date of Patent: Nov. 15, 2011

(54) METHOD FOR MAKING A FORMING STRUCTURE

(75) Inventors: Keith Joseph Stone, Fairfield, OH (US); Brian Francis Gray, Cincinnati, OH (US); Julie Ann O'Neil, Milan, IN (US); Timothy Paul Fiedeldey, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 2377 days.

(21) Appl. No.: 10/388,793

(22) Filed: Mar. 14, 2003

(65) Prior Publication Data

US 2004/0118811 A1    Jun. 24, 2004

Related U.S. Application Data

(63) Continuation of application No. 10/375,594, filed on Feb. 27, 2003, now abandoned, which is a continuation-in-part of application No. 10/324,181, filed on Dec. 20, 2002.

(51) Int. Cl.
*B29C 33/40* (2006.01)
*B23K 26/36* (2006.01)

(52) U.S. Cl. ........ 264/400; 264/482; 264/154; 264/156; 264/219

(58) Field of Classification Search .................. 264/154, 264/156, 400, 482, 1.37, 1.6, 25, 219
See application file for complete search history.

(56) References Cited

U.S. PATENT DOCUMENTS

| | | |
|---|---|---|
| 2,862,251 A | 12/1958 | Kalwaites |
| 4,151,240 A | 4/1979 | Lucas |
| 4,327,730 A | 5/1982 | Sorensen |
| 4,342,314 A | 8/1982 | Radel |
| 4,377,736 A * | 3/1983 | Daunt et al. ............ 219/121.68 |
| 4,456,570 A | 6/1984 | Thomas |
| 4,463,045 A | 7/1984 | Ahr |

(Continued)

FOREIGN PATENT DOCUMENTS

DE    198 17 237 A1    10/1999

(Continued)

OTHER PUBLICATIONS

PCT International Search Report dated Apr. 19, 2004.

(Continued)

*Primary Examiner* — Mathieu D. Vargot
(74) *Attorney, Agent, or Firm* — Amanda T. Barry; Andrew J. Hagerty; Gary J. Foose

(57) ABSTRACT

A method for making a forming structure. In one embodiment the method comprises the steps of (a) providing a base material having a thickness; (b) providing a laser source; (c) laser etching a plurality of spaced-apart apertures, each aperture extending through the entire thickness of the base material, such that the non-laser-etched portions of the base material define a continuous network; and (d) laser etching the continuous network to remove material in a pattern that defines a plurality of protrusions, each protrusion being generally columnar and pillar-like. The plurality of protrusions can be laser etched first, before laser etching the plurality of spaced-apart apertures. The base material can be cylindrical-shaped and the laser etching can be accomplished in a continuous process by rotating the cylindrical-shaped base material as a laser source is operatively translated while laser etching a path similar to "threads" of a screw.

34 Claims, 16 Drawing Sheets

U.S. PATENT DOCUMENTS

| | | | |
|---|---|---|---|
| 4,528,239 A | 7/1985 | Trokhan | |
| 4,591,523 A | 5/1986 | Thompson | |
| 4,601,868 A | 7/1986 | Radel | |
| 4,609,518 A | 9/1986 | Curro | |
| 4,629,643 A | 12/1986 | Curro | |
| 4,634,440 A | 1/1987 | Widlund | |
| 4,690,679 A | 9/1987 | Mattingly, III | |
| 4,695,422 A | 9/1987 | Curro | |
| 4,741,941 A | 5/1988 | Englebert et al. | |
| 4,778,644 A | 10/1988 | Curro | |
| 4,797,246 A | 1/1989 | Reinke et al. | |
| 4,806,303 A | 2/1989 | Bianco | |
| 4,839,216 A | 6/1989 | Curro | |
| 4,846,821 A | 7/1989 | Lyons | |
| 5,269,981 A | 12/1993 | Jameson | |
| 5,520,875 A | 5/1996 | Wnuk | |
| 5,567,376 A | 10/1996 | Turi | |
| 5,576,147 A | 11/1996 | Guckel et al. | |
| 5,585,017 A | 12/1996 | James | |
| 5,670,110 A | 9/1997 | Dirk | |
| 5,681,301 A * | 10/1997 | Yang et al. | 604/370 |
| 5,763,044 A | 6/1998 | Ahr et al. | |
| 5,800,760 A | 9/1998 | Takizawa et al. | |
| 5,822,833 A | 10/1998 | James | |
| 5,824,352 A | 10/1998 | Yang | |
| 5,827,597 A | 10/1998 | James | |
| 5,906,786 A | 5/1999 | James | |
| 5,914,184 A | 6/1999 | Morman | |
| 5,916,462 A | 6/1999 | James | |
| 5,944,974 A | 8/1999 | Fahrenberg et al. | |
| 5,997,986 A | 12/1999 | Turi | |
| 5,998,696 A | 12/1999 | Schone | |
| 6,022,607 A | 2/2000 | James | |
| 6,117,524 A | 9/2000 | Hisanaka | |
| 6,161,367 A | 12/2000 | Walter | |
| 6,228,462 B1 | 5/2001 | Lee | |
| 6,240,817 B1 | 6/2001 | James | |
| 6,300,258 B1 | 10/2001 | Stano | |
| 6,312,640 B1 | 11/2001 | Shimalla | |
| 6,417,426 B1 | 7/2002 | Takai | |
| 6,452,063 B1 | 9/2002 | Curro et al. | |
| 6,468,626 B1 | 10/2002 | Takai | |
| 6,479,130 B1 | 11/2002 | Takai | |
| 6,503,597 B2 | 1/2003 | Takai | |
| 6,503,598 B1 | 1/2003 | Goda | |
| 6,506,473 B1 | 1/2003 | Hisanaka | |
| 6,514,382 B1 | 2/2003 | Kakuichi et al. | |
| 6,548,158 B2 | 4/2003 | Mizutani | |
| RE38,105 E | 5/2003 | James | |
| 2001/0014796 A1 | 8/2001 | Mizutani | |
| 2004/0121120 A1 | 6/2004 | Gray et al. | |
| 2004/0247833 A1 | 12/2004 | Copat et al. | |
| 2005/0191496 A1 | 9/2005 | Gray et al. | |
| 2005/0209575 A1 | 9/2005 | Stone et al. | |

FOREIGN PATENT DOCUMENTS

| | | |
|---|---|---|
| EP | 0 304 617 B1 | 1/1995 |
| EP | 0 858 792 A2 | 8/1998 |
| EP | 0 862 904 A2 | 9/1998 |
| EP | 0 919 212 A2 | 6/1999 |
| EP | 1 036 871 A1 | 9/2000 |
| EP | 1036871 * | 9/2000 |
| EP | 1 062 927 A2 | 12/2000 |
| EP | 1 095 645 A2 | 5/2001 |
| EP | 1 110 526 A2 | 6/2001 |
| EP | 1 118 315 A2 | 7/2001 |
| EP | 1 121 916 A2 | 8/2001 |
| EP | 1 133 962 A1 | 9/2001 |
| EP | 1 138 299 A2 | 10/2001 |
| EP | 1 138 300 A2 | 10/2001 |
| EP | 1 283 019 A1 | 2/2003 |
| JP | 2 831 677 | 12/1998 |
| JP | 2001-105504 | 4/2001 |
| JP | 2001-129017 | 5/2001 |
| WO | WO 94/20054 | 9/1994 |
| WO | WO 97/00656 | 1/1997 |
| WO | WO 97/31601 A1 | 9/1997 |
| WO | WO 98/29071 A1 | 7/1998 |
| WO | WO 99/30658 A1 | 6/1999 |
| WO | WO 00/59431 A1 | 10/2000 |
| WO | WO 01/03626 A1 | 1/2001 |
| WO | WO 01/43969 A1 | 6/2001 |
| WO | WO 02/098338 A1 | 12/2002 |

OTHER PUBLICATIONS

Decision on Appeal Before the Board of Patent Appeals and Interferences, Ex parte Brian Francis Gray and Keith Joseph Stone, Appeal 2007-2198; U.S. Appl. No. 10/324,181, Technology Center 1700, Decided: Sep. 20, 2007.

U.S. Appl. No. 11/893,426, filed Aug. 16, 2007, Gray et al.

* cited by examiner

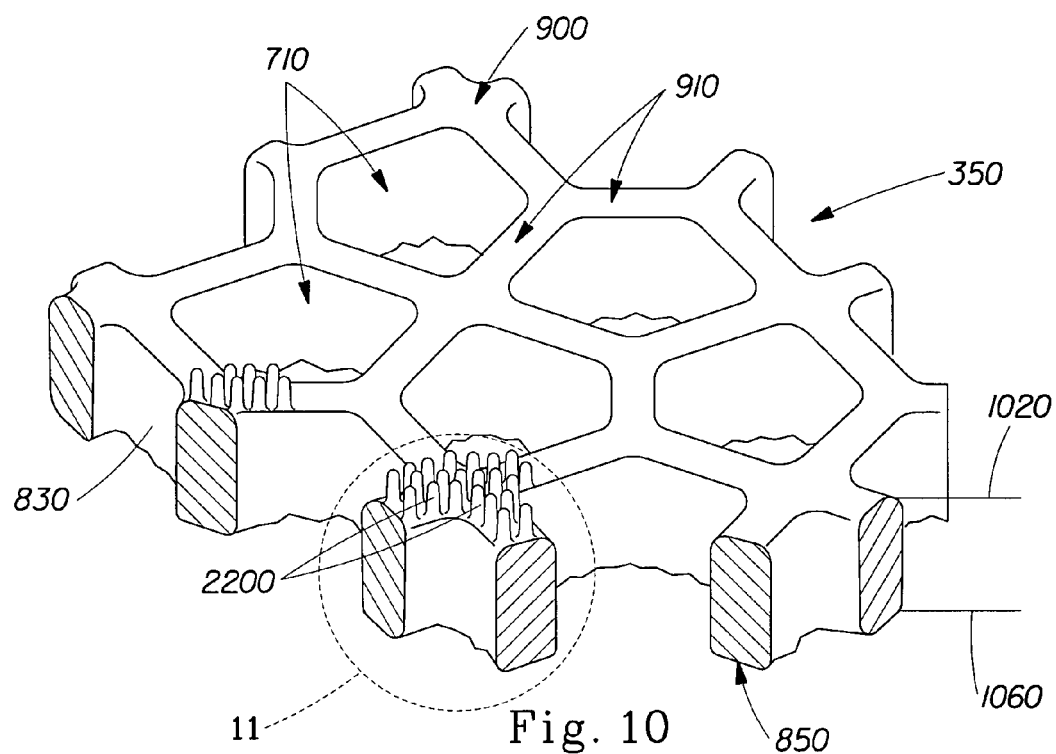
Fig. 10
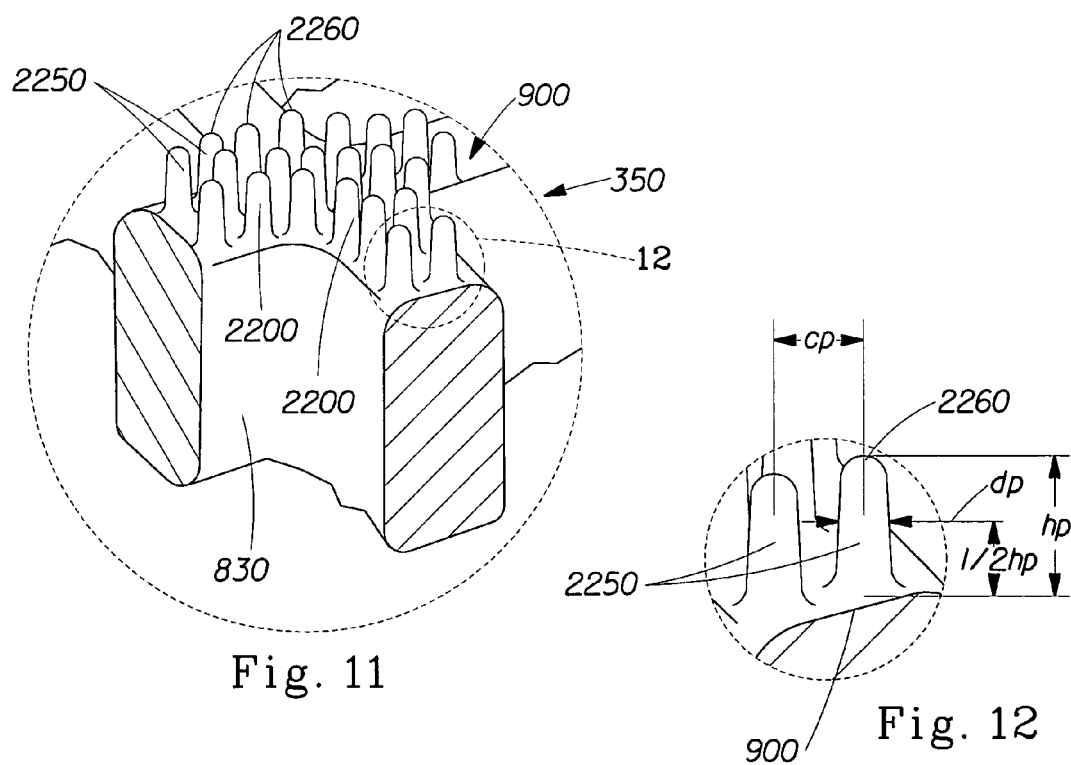
Fig. 11
Fig. 12

METHOD FOR MAKING A FORMING STRUCTURE

CROSS REFERENCE TO RELATED APPLICATION

This application is a continuation of U.S. patent application Ser. No. 10/375,594 entitled "Apparatus and Method for Making a Forming Structure", filed on Feb. 27, 2003, now abandoned which is a is a continuation-in-part of pending U.S. Ser. No. 10/324,181, filed on Dec. 20, 2002.

FIELD OF THE INVENTION

The present invention relates to a forming structure for making a polymeric web exhibiting a soft and silky tactile impression on at least one surface. More particularly, the present invention relates forming structure for making a three-dimensional polymeric web exhibiting a soft and silky tactile impression that can be used as a body-facing topsheet in disposable absorbent.

BACKGROUND OF THE INVENTION

It is extremely desirable to construct disposable articles, such as absorptive devices, including sanitary napkins, pantyliners, interlabial devices, diapers, training pants, incontinent devices, wound dressings and the like, with a soft cloth-like surface feel to the user's skin at any anticipated points of contact. Likewise, it has long been known in the disposable articles art to construct absorptive devices that present a dry surface feel to the user, especially during use. By having a soft, cloth-like body-facing surface that retains a dry surface feel during use, an absorptive device gives improved wearing comfort, and minimizes the development of undesirable skin conditions due to prolonged exposure to moisture absorbed within the absorptive device.

While woven and non-woven fibrous webs are often employed as body-facing topsheets for absorptive devices because of their pleasant surface feel, macroscopically expanded, three dimensional, apertured polymeric webs such as the commercially successful DRI-WEAVE™ topsheet marketed by Procter & Gamble Company have also been utilized. One viable polymeric web of this type is disclosed in U.S. Pat. No. 4,342,314 issued to Radel et al. on Aug. 3, 1982. Such webs have been shown to exhibit desirable fluid transport and fluid retaining characteristics. Desirable fluid transport characteristics allow the topsheet to acquire fluids, such as urine or menses, and pass to fluid into the absorptive article. Once absorbed into the absorptive article, the fluid retaining feature of the topsheet preferably prevents rewet, i.e., the movement of fluid back through the topsheet. Rewet can be a result of at least two causes: (1) squeezing out of the absorbed fluid due to pressure on the absorptive article; and/or (2) wetness entrapped within or on the topsheet. Preferably, both properties, fluid acquisition and fluid retention, are maximized. Said differently, preferably a topsheet will exhibit high rates of fluid acquisition, and low levels of rewet.

Other macroscopically expanded, three dimensional, apertured polymeric webs are known. For example, U.S. Pat. No. 4,463,045 issued to Ahr et al. on Jul. 31, 1984 discloses a macroscopically expanded three-dimensional polymeric web that exhibits a substantially non-glossy visible surface and cloth-like tactile impression. Ahr et al. teaches the criteria which must be met with respect to the regularly spaced pattern of surface aberrations in order to diffusely reflect incident light and thereby eliminate gloss. Ahr, et al teaches that the surface aberrations in the web should exhibit an average amplitude of at least about 0.2 mils (i.e., 0.0002 inches), and most preferably at least about 0.3 mils (i.e., 0.0003 inches) for a more clothlike or fiberlike tactile impression in the resultant web. Despite its advancements in eliminating gloss, the structure of the surface aberrations of the web in Ahr, et al. can lack desired softness. As recognized in the art, for example is U.S. Pat. No. 4,629,643, issued to Curro et al. (discussed below), the lack of desired softness is believed to be due to the structure of each aberration, which can be described as having the properties of an "arch" that behaves as a discrete structural unit, resisting deflection. This lack of sufficient deflection detracts from the softness impression experienced by the user's skin.

One proposed solution to improve the softness impression to the web of Ahr et al., was disclosed in the aforementioned U.S. Pat. No. 4,629,643 (Curro, et al. '643) Curro, et al. '643 discloses a microapertured polymeric web exhibiting a fine scale pattern of discrete surface aberrations. Each of these surface aberrations have a maximum amplitude and, unlike the web structure disclosed in Ahr, et al. at least one microaperature is provided that is substantially coincidental with the maximum amplitude of each surface aberration. The forming of microapertures at the maximum amplitude of each surface aberration provides a volcano-like cusp with petal shaped edges. It is believed that the resultant web surface that is in contact with the human skin is of smaller total area and is less resistant to compressive and shear forces than the unapertured "arch-like" structures taught by Ahr et al.

Although the microapertured film of Curro, et al. '643 imparts superior tactile impression to the skin of the user, it has some drawbacks related to certain fluid handling properties when used as a topsheet in absorbent articles. For example, it has been found that a web as disclosed in Curro, et al. '643, when used as a topsheet on a sanitary pad can permit an unacceptably high amount of rewet, i.e., fluid that returns back to the skin-facing surface of the topsheet after initially having passed through the topsheet to be absorbed by the sanitary napkin. In particular, it appears that a web according to Curro '643 can be more susceptible to rewet under pressure. This is because when such a product is used as a topsheet in a catamenial product, for example, absorbed fluid can be urged back out of the product through the many microapertures of the topsheet. It appears that each of the microapertures in the structure of Curro, et al. '643 can provide a pathway for fluid to escape from an underlying absorbent core in an absorbent article under the pressure of normal wearing conditions. These pathways in the web structures therefore cause decreased fluid retention and increased rewet in the absorbent structures.

Attempts at alleviating the shortcoming of Curro '643, i.e., attempts to both maximize softness and reduce rewet, can be found, for example, in U.S. Pat. No. 6,228,462 issued to Lee, et al., on May 8, 2001. Lee discloses a compression resistant web comprising rigid polymers. The compression resistance of the rigid polymers helps reduce rewet, but the rigid polymers utilized tend to decrease the softness of the web.

Furthermore, the hydroforming processes disclosed in Curro, et al. '643 and Lee '462 for making macroscopically expanded, three dimensional, apertured polymeric webs results in a formed film that must be dried after hydroforming. Due to the many interstices of the microapertures that can retain water, drying commercial quantities of these webs consumes significant amounts of energy, and can require significant capital investments in drying equipment. One example of an approach to effectively dry such webs is disclosed in U.S. Pat. No. 4,465,422 issued Sep. 22, 1987 to Curro, et al.

One further drawback associated with the webs disclosed in Curro '643 and Lee '462 when used as topsheets on sanitary napkins is the tendency of the microapertures to entrap fluid, such as menses. The entrapment can be in the microapertures themselves and/or between adjacent microapertures. Fluid so entrapped remains at or near the surface of the web, and can, therefore be in contact with the wearer's skin for prolonged periods of time. This contact negatively affects the skin health of the wearer and causes the topsheet to not have a clean appearance post-use.

Another attempt at making a soft, three-dimensional, macroscopically-expanded web having an improved functional surface is U.S. Pat. No. 5,670,110, issued to Dirk, et al. on Sep. 23, 1997. The web of Dirk et al. utilizes fibrils achieved via a screen printing roll. However, screen printing is a relatively slow process for making commercial webs for consumer articles.

Accordingly, it would be beneficial to have an improved formed film web that has superior tactile impression and superior fluid handling properties.

Additionally, it would be beneficial to have a formed film web that has superior tactile impression and provides for superior fluid retention and rewet characteristics.

Additionally, it would be beneficial to have a formed film web that has superior tactile impression and provides for superior cleanliness for hygiene articles.

Additionally, it would be beneficial to have an improved process for making a formed film web that has superior tactile impression and provides for superior fluid retention and rewet characteristics.

Finally, it would be beneficial to have an improved apparatus and method of making a forming structure for forming a formed film web that has superior tactile impression and provides for superior fluid retention and rewet characteristics.

SUMMARY OF THE INVENTION

A method for making a forming structure is disclosed. In one embodiment the method comprises the steps of:
 a) providing a base material having a thickness;
 b) providing a laser source;
 c) laser etching a plurality of spaced-apart apertures, each aperture extending through the entire thickness of the base material, such that the non-laser-etched portions of the base material define a continuous network; and
 d) laser etching the continuous network to remove material in a pattern that defines a plurality of protrusions, each protrusion being generally columnar and pillar-like.

In one embodiment the plurality of protrusions can be laser etched first, then the plurality of spaced-apart apertures. In another embodiment the base material is cylindrical-shaped and the laser etching of the apertures and/or the protrusions can be accomplished in a continuous process by rotating the cylindrical-shaped base material as a laser source is operatively translated while laser etching a path similar to "threads" of a screw.

BRIEF DESCRIPTION OF THE DRAWING

While the specification concludes with claims particularly pointing out and distinctly claiming the subject matter of the present invention, it is believed that the invention will be better understood from the following description taken in conjunction with the accompanying Figures, in which:

FIG. 10 is an enlarged, partially segmented, perspective illustration of a forming structure of the present invention.

FIG. 11 is a further enlarged, partial view of a portion of the forming structure shown in FIG. 10.

FIG. 12 is a further enlarged partial view of a portion of the forming structure shown in FIG. 11.

DETAILED DESCRIPTION OF THE INVENTION

Figure 1:
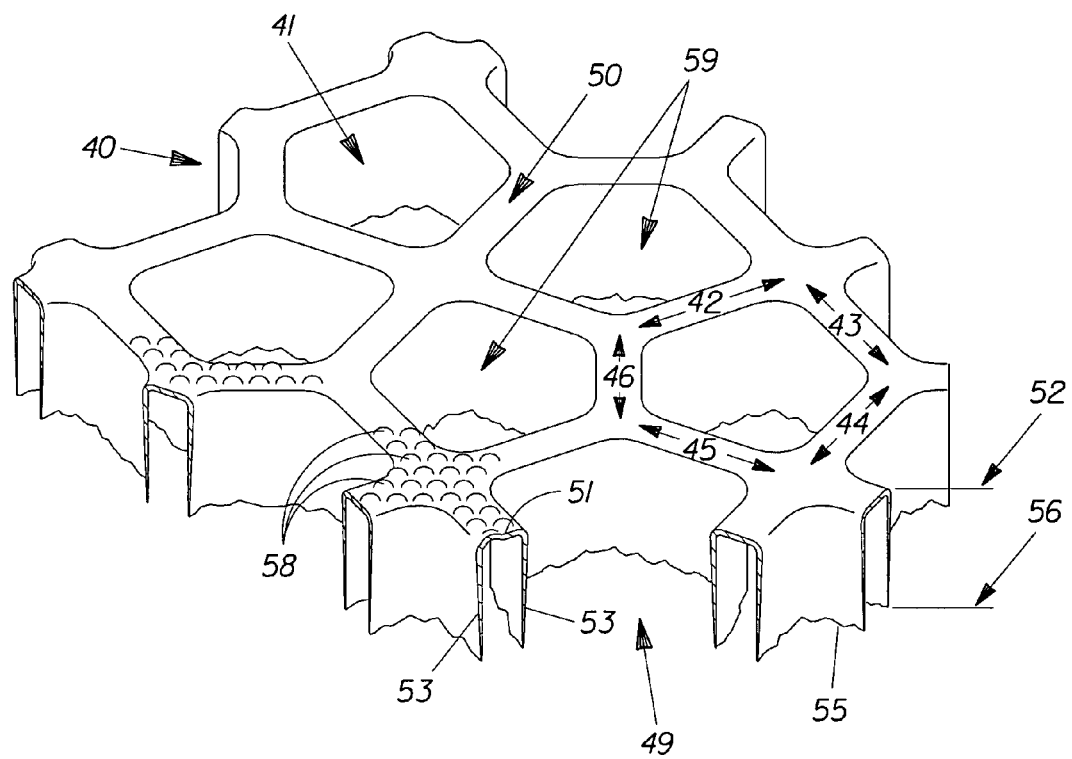
FIG. 1 is an enlarged, partially segmented, perspective illustration of a prior art polymeric web of the type generally disclosed in commonly assigned U.S. Pat. No. 4,342,314.

FIG. 1 is an enlarged, partially segmented perspective illustration of a prior art macroscopically-expanded, three-dimensional, fluid pervious polymeric web 40 formed generally in accordance with the aforementioned U.S. Pat. No. 4,342,314. Webs of this type have been found to be highly suitable for use as a topsheet in absorbent articles such as sanitary napkins, pantyliners, interlabial devices, and the like. The fluid pervious web 40 exhibits a plurality of macroscopic surface aberrations that can be apertures, such as primary apertures 41. Primary apertures 41 are formed by a multiplicity of interconnecting members, such as fiber like elements, e.g., 42, 43, 44, 45 and 46, that are interconnected to one another to define a continuous first surface 50 of the web 40. Each fiber like element has a base portion, e.g., base portion 51, located in plane 52 of first surface 50. Each base portion has a sidewall portion, e.g., sidewall portion 53, attached to each longitudinal edge thereof. The sidewall portions extend generally in the direction of a discontinuous second surface 55 of web 40. The intersecting sidewall portions are interconnected to one another intermediate the first and second surfaces of the web, and terminate substantially concurrently with one another in the plane 56 of the second surface 55. In some embodiments, the base portion 51 may have surface aberrations 58 in accordance with the aforementioned Ahr '045 patent.

As used herein, the term "macroscopically expanded" refers to the structure of a web formed from a precursor web or film, e.g., a planar web, that has been caused to conform to the surface of a three-dimensional forming structure so that both sides, or surfaces, of the precursor web are permanently altered due to at least partial conformance of the precursor web to the three-dimensional pattern of the forming structure. Such macroscopically-expanded webs are typically caused to conform to the surface of the forming structure by embossing (i.e., when the forming structure exhibits a pattern comprised primarily of male projections), by debossing (i.e., when the forming structure exhibits a pattern comprised primarily of female depressions, or apertures), or by a combination of both.

As used herein, the term "macroscopic" refers to structural features or elements that are readily visible and distinctly discernable to a human having 20/20 vision when the perpendicular distance between the viewer's eye and the web is about 12 inches. Conversely, the term "microscopic" is utilized to refer to structural features or elements that are not readily visible and distinctly discernable to a human having 20/20 vision when the perpendicular distance between the viewer's eye and the plane of the web is about 12 inches. In general, as used herein, the primary apertures of a web disclosed herein are macroscopic, and surface aberrations, such as hair-like fibrils as disclosed more fully below are considered microscopic.

The term "planar" as used herein to refers to the overall condition of a precursor web or film when viewed by the naked eye on a macroscopic scale, prior to permanently deforming the web into a three-dimensional formed film. In this context, extruded films prior to post-extrusion processing and films that do not exhibit significant degree of permanent macroscopic three-dimensionality, e.g., deformation out of the plane of the film, would generally be described as planar.

As utilized herein, the term "interconnecting members" refers to some or all of the elements of a web, e.g., web 40 in FIG. 1, portions of which serve to define the primary apertures by a continuous network. As can be appreciated from the description of FIG. 1 and the present invention herein, the interconnecting members, e.g., fiber like elements 42, 43, 44, 45, and 46, are inherently continuous, with contiguous interconnecting elements blending into one another in mutually adjoining transition portions. Individual interconnecting members can be best described with reference to FIG. 1 as those portions of the web disposed between any two adjacent primary apertures, originating in the first surface and extending into the second surface. On the first surface of the web the interconnecting members collectively form a continuous network, or pattern, the continuous network of interconnecting members defining the primary apertures, and on the second surface of the web interconnecting sidewalls of the interconnecting members collectively form a discontinuous pattern of secondary apertures. Interconnecting members are described more generally below with reference to FIG. 6.

In a three-dimensional, macroscopically-expanded web, the interconnecting members may be described as channel-like. Their two dimensional cross-section may also be described as "U-shaped", as in the aforementioned Radel '314 patent, or "upwardly concave-shaped", as disclosed in U.S. Pat. No. 5,514,105, issued on May 7, 1996 to Goodman, Jr., et al. "Upwardly-concave-shaped" as used herein, and as represented in FIG. 1, describes the orientation of the channel-like shape of the interconnecting members with relation to the surfaces of the web, with a base portion 51 generally in the first surface 50, and the legs, e.g., sidewall portions 53, of the channel extending from the base portion 51 in the direction of the second surface 55, with the channel opening being substantially in the second surface 55. In general, for a plane cutting through the web, e.g., web 40, orthogonal to the plane, e.g., plane 52, of the first surface 50 and intersecting any two adjacent primary apertures, e.g., apertures 41, the resulting cross-section of an interconnecting member disposed therein will exhibit a generally upwardly concave shape that may be substantially U-shaped.

The term "continuous" when used herein to describe the first surface of a macroscopically-expanded, three-dimensional formed film web, refers to the uninterrupted character of the first surface generally in the plane of the first surface. Thus, any point on the first surface can be reached from any other point on the first surface without substantially leaving the first surface. Conversely, as utilized herein, the term "discontinuous" when used to describe the second surface of a three-dimensionally formed film web refers to the interrupted character of the second surface generally in the plane of the second surface. Thus, any point on the second surface cannot necessarily be reached from any other point on the second surface without substantially leaving the second surface in the plane of the second surface.

Figure 2:
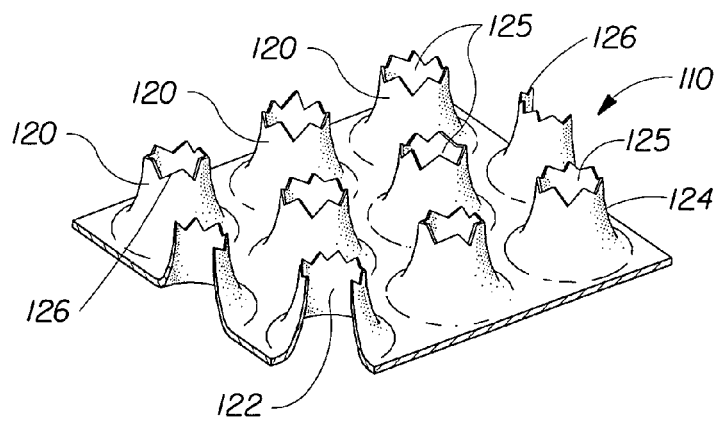
FIG. 2 is an enlarged, partially segmented, perspective illustration of a prior art polymeric web of the type generally disclosed in commonly assigned U.S. Pat. No. 4,629,643.

FIG. 2 shows an enlarged, partially segmented, perspective illustration of a portion of another prior art polymeric microapertured web 110 formed generally in accordance with the aforementioned Curro '643 patent. The microapertured surface aberrations 120 can be formed by a hydroforming process in which a high-pressure liquid jet is utilized to force the web to conform to a three-dimensional support member. As shown, ruptures which coincide substantially with the maximum amplitude of each micropertured surface aberration 120 result in the formation of a volcano-shaped aperture 125 having relatively thin, irregularly shaped petals 126 about its periphery. The relatively thin, petal-shaped edges of the aperture of such a web provide for increased softness impression on the skin of a user when compared, for example, to the web of Ahr '045. It is believed that this softness impression is due to the relative lack of resistance to compression and shear afforded by the surface aberrations having volcano-shaped apertures.

As mentioned above, although the microapertured film of Curro '643 imparts a superior tactile impression of softness, it can also permit undesirable rewet when used as a topsheet on a disposable absorbent article. The web of the present invention solves this problem by providing for softness via surface aberrations that exhibit low resistance to compression and shear, comparable to the web of Curro '643, and yet do not permit fluid flow via microapertures. Therefore, one benefit of the web of the present invention is superior softness together with minimal rewet when used as a topsheet on a disposable absorbent article, such as a sanitary napkin.

Figure 3:
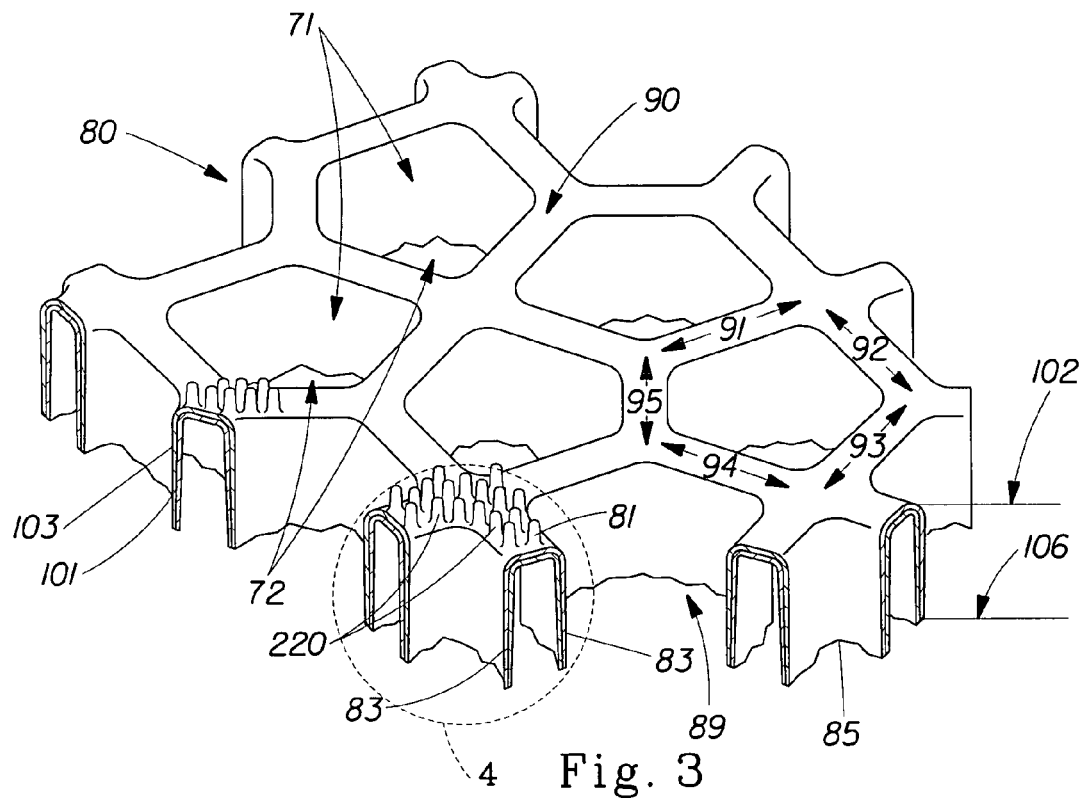
FIG. 3 is an enlarged, partially segmented, perspective illustration of a polymeric web made on a forming structure of the present invention.

FIG. 3 is an enlarged, partially segmented perspective illustration of a fluid pervious, macroscopically-expanded, three-dimensional polymeric web 80 of the present invention. The geometric configuration of the macroscopic surface aberrations, e.g., primary apertures 71, of the polymeric web can be generally similar to that of the prior art web 40 illustrated in FIG. 1. Primary apertures 71 may be referred to as "apertures" or "macroapertures" herein, and refer to openings in the web that permit fluid communication between a first surface 90 of web 80 and a second surface 85 of web 80. The primary apertures 71 of the web shown in FIG. 3 are defined in the plane 102 of first surface 90 by a continuous network of interconnecting members, e.g., members 91, 92, 93, 94, and 95 interconnected to one another. The shape of primary apertures 71 as projected in the plane of the first surface 90 may be in the shape of polygons, e.g., squares, hexagons, etc., in an ordered or random pattern. In a preferred embodiment primary apertures 71 are in the shape of modified ovals, and in one embodiment primary apertures 71 are in the general shape of a tear drop. Polymer web 80 exhibits a plurality of surface aberrations 220 in the form of hair-like fibrils 225, described more fully below.

In a three-dimensional, microapertured polymeric web 80 of the present invention, each interconnecting member comprises a base portion, e.g., base portion 81, located generally in plane 102, and each base portion has sidewall portions, e.g., sidewall portions 83 extending from each longitudinal edge thereof. Sidewall portions 83 extend generally in the direction of the second surface 85 of the web 80 and join to sidewalls of adjoining interconnecting members intermediate the first and second surfaces, 90 and 85, respectively, and terminate substantially concurrently with one another to define secondary apertures, e.g., secondary apertures 72 in the plane 106 of second surface 85.

Figure 6:
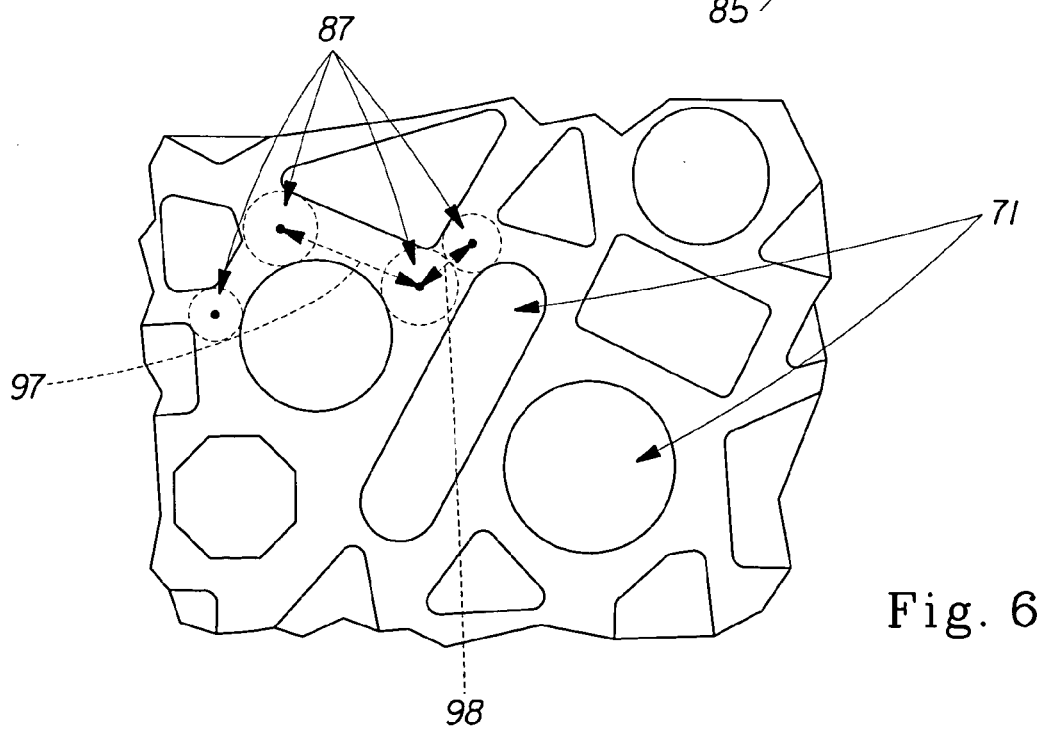
FIG. 6 is a plan view of representative aperture shapes projected in the plane of the first surface of a polymeric web of the present invention.

FIG. 6 is a plan view of representative primary aperture shapes projected in the plane of the first surface of an alternative embodiment of a three-dimensional, macroapertured polymer web of the present invention. While a repeating pattern of uniform shapes, for example a tessellating pattern, is preferred, the shape of primary apertures, e.g., apertures 71, may be generally circular, polygonal, or mixed, and may be arrayed in an ordered pattern or in a random pattern.

As shown in FIG. 6 the interconnecting members, e.g., interconnecting members 97 and 98, are each inherently continuous, with contiguous interconnecting elements blending into one another in mutually adjoining transition zones or portions, e.g., portions 87. In general transition portions are defined by the largest circle that can be inscribed tangent to any three adjacent apertures. It is understood that for certain patterns of apertures the inscribed circle of the transition portions may be tangent to more than three adjacent apertures. For illustrative purposes, interconnecting members may be thought of as beginning or ending substantially at the centers of the transition portions, such as interconnecting members 97 and 98. Interconnecting members need not be linear, but may be curvilinear. The sidewalls of the interconnecting members can be described as interconnecting to the sidewalls of adjacent, contiguous interconnecting members. Exclusive of portions of the transition zones and portions including hair-like fibrils, as disclosed below, cross-sections of interconnecting members transverse to the longitudinal centerline between the beginning and end of the interconnecting member may be generally described as U-shape. However, the transverse cross-section need not be uniform or U-shaped along the entire length of the interconnecting member, and for certain primary aperture configurations it may not be uniform along most of its length. In particular, in transition zones or portions interconnecting members blend into contiguous interconnecting members and transverse cross-sections in the transition zones or portions may exhibit substantially non-uniform U-shapes, or no discernible U-shape.

Figure 4:
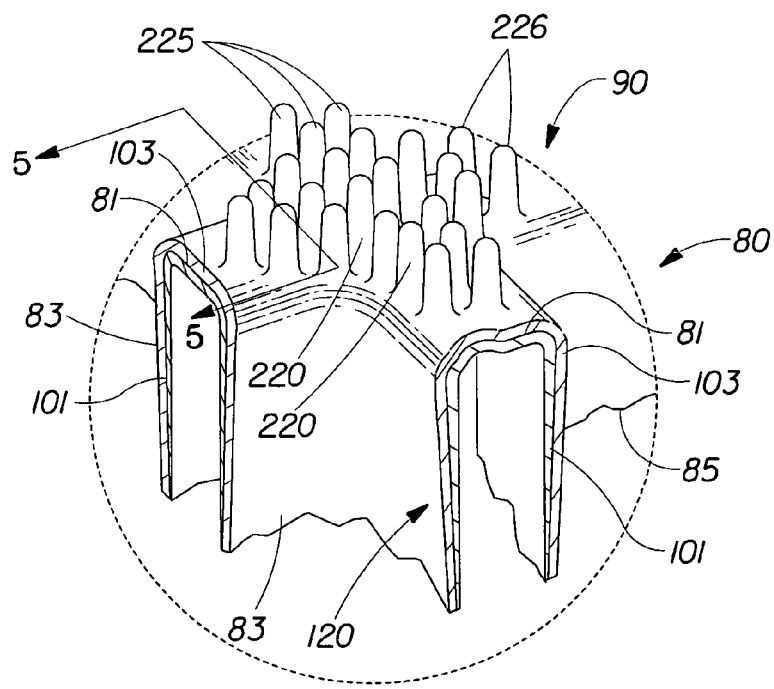
FIG. 4 is a further enlarged, partial view of a portion of the web shown in FIG. 3 illustrating in greater detail certain features of the polymeric web of the present invention.

FIG. 4 is a further enlarged, partial view of the three-dimensional polymeric web 80 shown in FIG. 3. The three-dimensional polymeric web 80 comprises a polymer film 120, i.e., the precursor film, which can be a single layer of extruded polymer or a multilayer coextruded or laminate film. As shown in FIG. 4, film 120 is a two layer laminate comprising a first layer 101 and a second layer 103. Laminate materials may be coextruded, as is known in the art for making laminate films, including films comprising skin layers. While it is presently preferred that, as shown in FIG. 4, the polymeric layers, e.g., layers 101 and 103, terminate substantially concurrently in the plane of the second surface 106 it is not presently believed to be essential that they do so. One or more layers may extend further toward the second surface than the other(s).

FIG. 4 shows a plurality of surface aberrations 220 in the form of hair-like fibrils 225. The hair-like fibrils are formed as protruded extensions of the polymeric web 80, generally on the first surface 90 thereof. The number, size, and distribution of hair-like fibrils 225 on polymeric web 80 can be predetermined based on desired skin feel. For applications as a topsheet in disposable absorbent articles, it is preferred that hair-like fibrils 225 protrude only from the base portion 81 in first surface 90 of polymeric web 80, as shown in FIGS. 3 and 4. Therefore, when web 80 is used as a topsheet in a disposable absorbent article, the web can be oriented such that the hair-like fibrils 225 are skin contacting for superior softness impression, and yet, the hair-like fibrils 225 do not obstruct fluid flow through macroapertures 71. Moreover, having hair-like fibrils 225 with closed distal portions 226 results in reduced rewet, i.e., reduced amounts of fluid being re-introduced to the surface of the topsheet after having been first passed through the topsheet to underlying absorbent layers.

Figure 5:
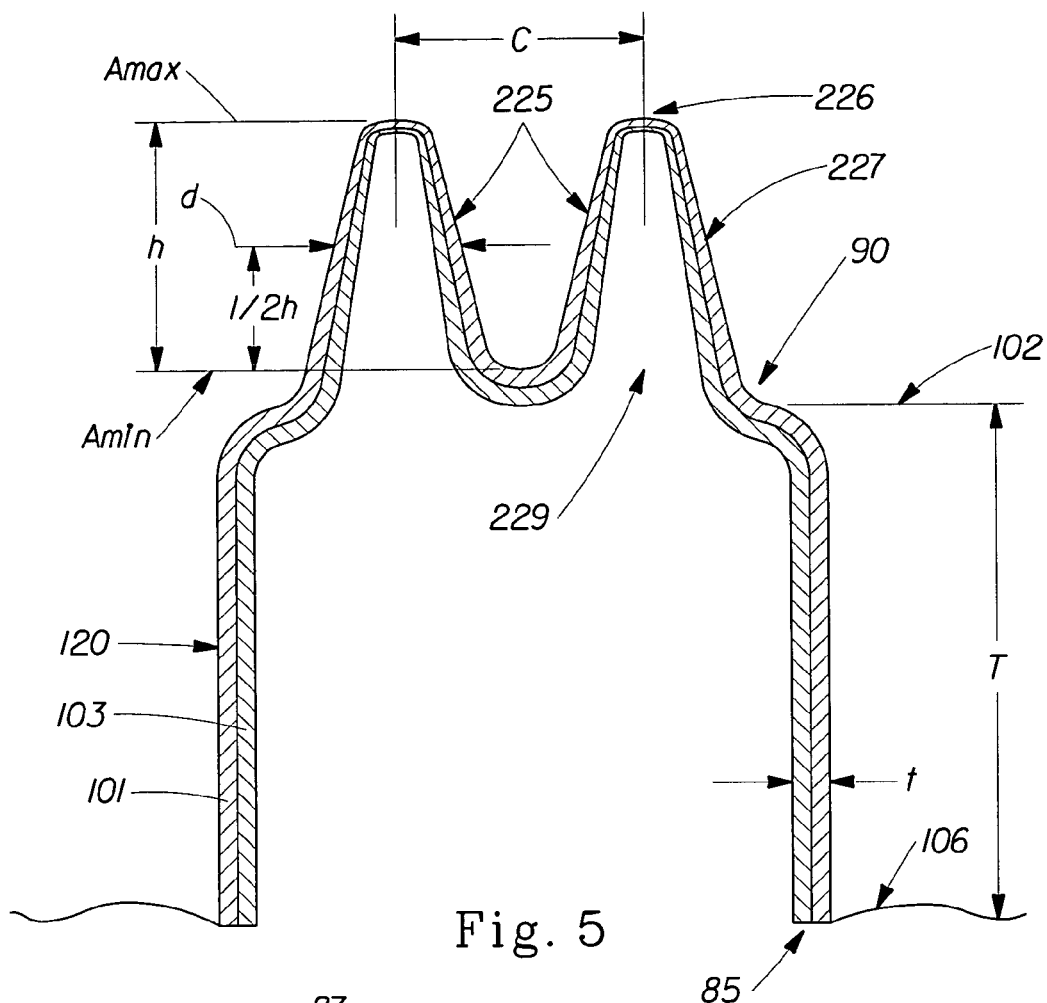
FIG. 5 is a cross-sectional depiction of a cross section taken along Section 5-5 of FIG. 4.

As shown in cross-section FIG. 5, hair-like fibrils 225 can be described as protruding from first surface 90 of web 80. As such, hair-like fibrils 225 can be described as being integral with film 120, and formed by permanent local plastic deformation of film 120. Hair-like fibrils can be described as having a sidewall 227 defining an open proximal portion 229 and a closed distal portion 226. Hair-like fibrils 225 have a height h measured from a minimum amplitude $A_{min}$ between adjacent fibrils to a maximum amplitude $A_{max}$ at the closed distal portion 226. Hair-like fibrils have a diameter d, which for a generally cylindrical structure is the outside diameter at a lateral cross-section. By "lateral" is meant generally parallel to the plane of the first surface 102. For non-uniform lateral cross-sections, and/or non-cylindrical structures of hair-like fibrils, diameter d is measured as the average lateral cross-sectional dimension at ½ the height h of the fibril, as shown in FIG. 5. Thus, for each hair-like fibril 225, an aspect ratio, defined as h/d, can be determined. Hair-like fibrils 225 can have an aspect ratio h/d of at least 0.5. The aspect ratio can be 1, or 1.5 and is preferably at least about 2.

In general, because the actual height h of any individual hair-like fibril 225 can be difficult to determine, and because the actual height may vary, an average height $h_{avg}$ of a plurality of hair-like fibrils can be determined by determining an average minimum amplitude $A_{min}$ and an average maximum amplitude $A_{max}$ over a predetermined area of web 80. Likewise, for varying cross-sectional dimensions, an average dimension $d_{avg}$ can be determined for a plurality of hair-like fibrils 225. Such amplitude and other dimensional measurements can be made by any method known in the art, such as by computer aided scanning microscopy and data processing. Therefore, an average aspect ratio $AR_{avg}$ of the hair-like fibrils 225 for a predetermined portion of the web can be expressed as $h_{avg}/d_{avg}$.

The dimensions h and d for hair-like fibrils 225 can be indirectly determined based on the known dimensions of a forming structure, as disclosed more fully below. For example, for a forming structure made according to predetermined dimensions of male protrusions, e.g., protrusions 2250 shown in FIG. 11 below, on which hair-like fibrils 225 are to be formed can have known dimensions. If precursor film 120 is fully and permanently deformed over protrusions 2250, then h and d can be calculated from these known dimensions, taking into account the thickness of the precursor film 120, including predicted and/or observed web thinning. If the precursor film 120 is not fully formed over protrusions 2250, then the height h of hair-like pillars will be less than the corresponding height of the protrusions 2250.

In one embodiment the diameter of hair-like fibrils 225 is constant or decreases with increasing amplitude (amplitude increases to a maximum at closed distal end 226). As shown in FIG. 5, for example, the diameter, or average lateral cross-sectional dimension, of hair-like fibrils 225 can be a maximum at proximal portion 229 and the lateral cross-sectional dimension steadily decreases to distal end 226. This structure is believed to be necessary to ensure the polymeric web 80 can be readily removed from the forming structure 350, as more fully described below with respect to FIG. 10.

As shown in FIG. 5, some thinning of precursor web 120 can occur due to the relatively deep drawing required to form high aspect ratio hair-like fibrils 225. For example, thinning can be observed at or near closed distal ends 226. By "observed" is meant that the thinning is distinct when viewed in magnified cross-section. Such thinning can be beneficial as the thinned portions offer little resistance to compression or shear when touched by a person's skin. For example, when a person touches the polymeric web 80 on the side exhibiting hair-like fibrils 225, the finger tips first contact closed distal ends 226 of hair-like fibrils 225. Due to the high aspect ratio of hair-like fibrils 225, and, it is believed, to the wall thinning of the film at or near the distal ends 226, the hair-like fibrils offer little resistance to the compression or shear imposed on the web by the person's fingers. This lack of resistance is registered as a feeling of softness, much like the feeling of a velour fabric. In fact, it has been found that polymeric webs of the present invention can provide for a feeling of softness equal to or greater than that of prior art polymeric webs, such as the web disclosed in Curro '643.

It should be noted that a fluid impermeable web having only the hair-like fibrils as disclosed herein, and not having macroscopic apertures, can offer softness for any application in which fluid permeability is not required. Thus, in one embodiment of the present invention, the invention can be described as a polymeric web 80 exhibiting a soft and silky tactile impression on at least one surface thereof, the silky feeling surface of the web 80 exhibiting a pattern of discrete hair-like fibrils 225, each of the hair-like fibrils 225 being a protruded extension of the web surface and having a side wall 227 defining an open proximal portion 229 and a closed distal portion 226, the hair-like fibrils maximum lateral cross-sectional dimension at or near said open proximal portion, exhibiting a cross-sectional diameter d of between about 50 microns (about 0.002 inch) to about 76 microns (about 0.003 inch), and can be at least 100 microns (0.004 inches) 130 microns (0.005 inches). The hair-like fibrils can have an aspect ratio from 0.5 to 3.

For disposable absorbent articles, where a topsheet having a fluid permeable, three-dimensional structure is desired, the invention can be described as a polymeric web 80 exhibiting a soft and silky tactile impression on at least one surface 90 thereof, the silky feeling surface 90 of the web exhibiting a pattern of discrete hair-like fibrils 225, each of the hair-like fibrils 225 being a protruded extension of the web surface 90 and having a side wall 227 defining an open proximal portion 229 and a closed distal portion 226, the hair-like fibrils exhibiting an average cross-sectional diameter d of between 50 microns (0.002 inches) 130 microns (0.005 inches), and an aspect ratio from at least 0.5, 1, 1.5, 2, or 3 and wherein the web 80 further exhibits a macroscopically expanded, three-dimensional pattern of macroscopic surface aberrations, e.g., primary apertures 71 superposed thereon, the macroscopic surface aberrations 71 being oppositely oriented from the hair-like fibrils 225, that is, the primary apertures extend from a first surface 90 to a second surface 85 of polymeric web 80.

The "area density" of the hair-like fibrils 225, which is the number of hair-like fibrils 225 per unit area of first surface 90, can be optimized for use in absorbent articles. In general, the center-to-center spacing can be optimized for adequate tactile impression, while at the same time minimizing fiber-to-fiber entrapment of fluid. Currently, it is believed that a center-to-center spacing of about 100 microns to 250 microns (about 0.004 inch to about 0.010 inch) is optimal for use in sanitary napkins. Minimizing entrapment of menses between fibers improves the surface cleanliness of the sanitary napkin, which, in turn improves the cleanliness and skin health of the wearer.

In one embodiment, "superposed thereon" means that the polymeric web appears generally as shown in FIG. 3, wherein the pattern of discrete hair-like fibrils 225 is disposed on the land areas 81 of the interconnecting members only, i.e., only on the first surface 90 of web 80. However, conceptually, it is contemplated that "superposed thereon" could also cover an embodiment (not shown) in which the pattern of discrete hair-like fibrils 225 extends into macroapertures 71, for example on side walls 83 of the interconnecting members. In other embodiments, hair-like fibrils 225 are disposed only in certain predetermined regions of web 80. For example, a topsheet for a sanitary napkin can have a central region having hair-like fibrils 225, and the remainder of the topsheet being free from hair-like fibrils 225.

Precursor web 120 can be any polymeric film having sufficient material properties to be formed into the web of the present invention by the hydroforming process described herein. That is, precursor web 120 must have sufficient yield properties such that the precursor web 120 can be strained without rupture to an extent to produce hair-like fibrils 225 and, in the case of a three-dimensional, macroscopically-apertured, formed film, rupture to form macroapertures 71. As disclosed more fully below, process conditions such as temperature can be varied for a given polymer to permit it to stretch with or without rupture to form the web of the present invention. In general, therefore, it has been found that preferred starting materials to be used as the precursor web 120 for producing the web 80 of the present invention exhibit a low yield and high-elongation characteristics. In addition, the starting films preferably strain harden. Examples of films suitable for use as the precursor web 120 in the present invention include films of low density polyethylene (LDPE), linear low-density polyethylene (LLDPE), and blends of linear low-density polyethylene and low density polyethylene (LDPE/LLDPE).

Precursor web 120 must also be sufficiently deformable and have sufficient ductility for use as a polymeric web of the present invention. The term "deformable" as used herein describes a material which, when stretched beyond its elastic limit, will substantially retain its newly formed conformation.

One material found suitable for use as a precursor web 120 of the present invention is DOWLEX 2045A polyethylene resin, available from The Dow Chemical Company, Midland, Mich., USA. A film of this material having a thickness of 20 microns can have a tensile yield of at least 12 MPa; an ultimate tensile of at least 53 MPa; an ultimate elongation of at least 635%; and a tensile modulus (2% Secant) of at least 210 MPa (each of the above measures determined according to ASTM D 882).

Precursor web 120 can be a laminate of two or more webs, and can be a co-extruded laminate. For example, precursor web 120 can comprise two layers as shown in FIG. 4, and precursor web 120 can comprise three layers, wherein the inner most layer is referred to as a core layer, and the two outermost layers are referred to as skin layers. In one embodiment precursor web 120 comprises a three layer coextruded laminate having an overall thickness of about 25 microns (0.001 in.), with the core layer having a thickness of about 18 microns (0.0007 in.); and each skin layer having a thickness of about 3.5 microns (0.00015 in.). In general, for use as a topsheet in sanitary napkins, precursor web 120 should have an overall thickness (sometimes referred to as caliper) of at least about 10 microns and less than about 100 microns. The thickness of precursor web 120 can be about 15 microns, 20 microns, 25 microns, 30 microns, 35 microns, 40 microns, 45 microns, or 60 microns. In general, the ability to form high area density (or low average center-to-center spacing C) hair-like fibrils 225 on web 80 is limited by the thickness of precursor web 120. For example, it is believed that the center-to-center spacing C of two adjacent hair-like fibrils 225 should be greater than twice the thickness of precursor web 120 to permit adequate and complete three-dimensional web formation between adjacent protrusions 2250 of forming structure 350 as disclosed more fully below.

The precursor web 120 preferably comprises a surfactant. In a three layer laminate, the core layer can comprise a surfactant while the outer layers are initially devoid of surfactants. Preferred surfactants include those from non-ionic families such as: alcohol ethoxylates, alkylphenol ethoxylates, carboxylic acid esters, glycerol esters, polyoxyethylene esters of fatty acids, polyoxyethylene esters of aliphatic carboxylic acids related to abietic acid, anhydrosorbitol esters, etyhoxylated anhydrosorbitol esters, ethoxylated natural fats, oils, and waxes, glycol esters of fatty acids, carboxylic amides, diethanolamine condensates, and polyalkyleneoxide block copolymers. Molecular weights of surfactants selected for the present invention may range from about 200 grams per mole to about 10,000 grams per mole. Preferred surfactants have a molecular weight from about 300 to about 1,000 grams per mole.

The surfactant level initially blended into precursor web 120 (or optionally the core layer in a three layer laminate) can be as much as 10 percent by weight of the total multilayer structure. Surfactants in the preferred molecular weight range (300-1,000 grams/mole) can be added at lower levels, generally at or below about 5 weight percent of the total multilayer structure.

The precursor web 120 can also comprise titanium dioxide in the polymer blend. Titanium dioxide can provide for greater opacity of the finished web 80. Titanium dioxide can be added at up to about 10 percent by weight to low density polyethylene for blending into the precursor web 120 material.

Other additives, such as particulate material, e.g., calcium carbonate ($CaCO_3$), particulate skin treatments or protectants, or odor-absorbing actives, e.g., zeolites, can be added in one or more layers of precursor web 120. In some embodiments, webs 80 comprising particulate matter, when used in skin-contacting applications, can permit actives to contact the skin in a very direct and efficient manner. Specifically, in some embodiments, formation of hair-like fibrils 225 can expose particulate matter at or near the distal ends thereof. Therefore, actives such as skin care agents can be localized at or near distal ends 226 to permit direct skin contact with such skin care agents when the web 80 is used in skin contacting applications.

The precursor web 120 can be processed using conventional procedures for producing multilayer films on conventional coextruded film-making equipment. Where layers comprising blends are required, pellets of the above described components can be first dry blended and then melt mixed in the extruder feeding that layer. Alternatively, if insufficient mixing occurs in the extruder, the pellets can be first dry blended and then melt mixed in a pre-compounding extruder followed by repelletization prior to film extrusion. Suitable methods for making precursor web 120 are disclosed in U.S. Pat. No. 5,520,875, issued to Wnuk et al. on May 28, 1996 and U.S. Pat. No. 6,228,462, issued to Lee et al. on May 8, 2001; both patents the disclosure of which is incorporated herein by reference.

A fluid pervious polymeric web of the present invention can be utilized as a topsheet on a catamenial device, such as a sanitary napkin. For example, a polymeric web 80 of the present invention exhibiting a macroscopically expanded, three-dimensional pattern of macroscopic surface aberrations in the form of primary apertures 71 combines softness properties with excellent fluid rewet properties (i.e., reduced fluid rewet compared to previous webs, such as the web of Curro '643).

Figure 7:
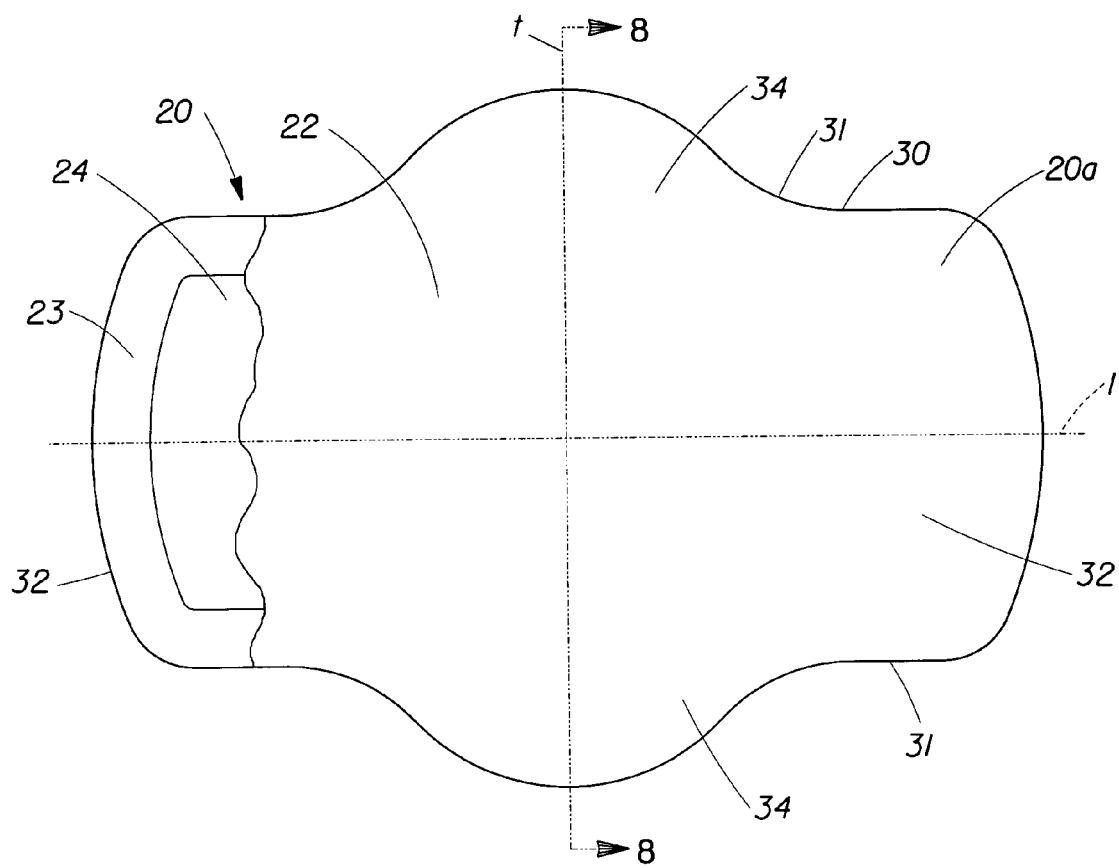
FIG. 7 is a top plan view of a sanitary napkin with portions cut away to more clearly show the construction of a catamenial device of the present invention.

FIG. 7 is a top plan view of a sanitary napkin 20 with portions cut away to more clearly show the construction of the napkin 20, including topsheet 22, which can comprise a polymeric web 80 of the present invention. It should be understood that the polymeric web 80 of the present invention can also be utilized in other absorbent articles such as pantyliners, interlabial devices, diapers, training pants, incontinent devices, wound dressings and the like. It also should be understood, that the present invention is not limited to the particular type or configuration of the sanitary napkin 20 shown in FIG. 7, which is simply a representative non-limiting example.

Figure 8:
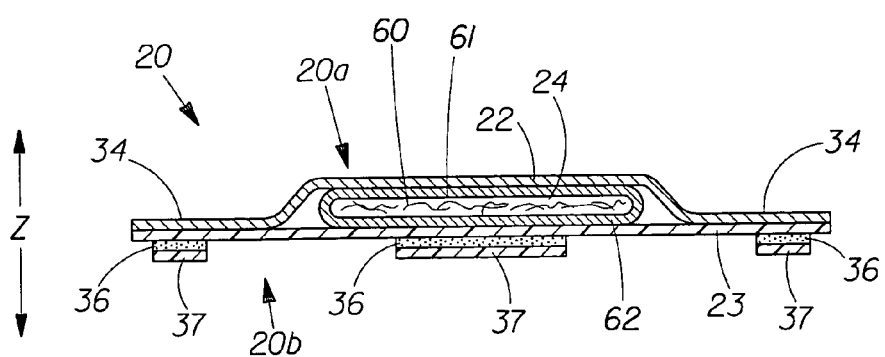
FIG. 8 is a cross-sectional view of the sanitary napkin taken along Section 8-8 of FIG. 7.

As shown in FIG. 8, the sanitary napkin 20 has two surfaces, a body-facing surface 20a and an opposed garment-facing surface 20b. The body-facing surface 20a is intended to be worn adjacent to the body of the wearer. The garment-facing surface 20b is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

As shown in FIG. 7, the sanitary napkin 20 comprises a liquid pervious topsheet 22, which can comprise web 80 of the present invention, a liquid impervious backsheet 23 joined with the liquid pervious topsheet 22, and an absorbent core 24 positioned between the liquid pervious topsheet 22 and the liquid impervious backsheet 23. FIG. 7 also shows that the sanitary napkin 20 has a periphery 30 which is defined by the outer edges of the sanitary napkin 20 in which the longitudinal edges (or "side edges") are designated 31 and the end edges (or "ends") are designated 32.

Sanitary napkin 20 preferably includes optional sideflaps or "wings" 34 that can be folded around the crotch portion of the wearer's panties. The side flaps 34 can serve a number of purposes, including, but not limited to protecting the wearer's panties from soiling and keeping the sanitary napkin secured to the wearer's panties.

FIG. 8 is a cross-sectional view of the sanitary napkin taken along section line 8-8 of FIG. 7. As can be seen in FIG. 8, the sanitary napkin 20 preferably includes adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use. In addition to having a longitudinal direction and a transverse direction, the sanitary napkin 20 also has a "z" direction or axis, which is the direction proceeding down through the liquid pervious topsheet 22 and into whatever fluid storage core 24 that may be provided. A continuous path between the liquid pervious topsheet 22 and underlying layer or layers of the articles herein permits fluid to be drawn in the "z" direction and away from the topsheet of the article into its ultimate storage layer. In some embodiments, the continuous path will have a gradient of increasing capillary attraction, which facilitates fluid flow down into the storage medium.

Figure 9:
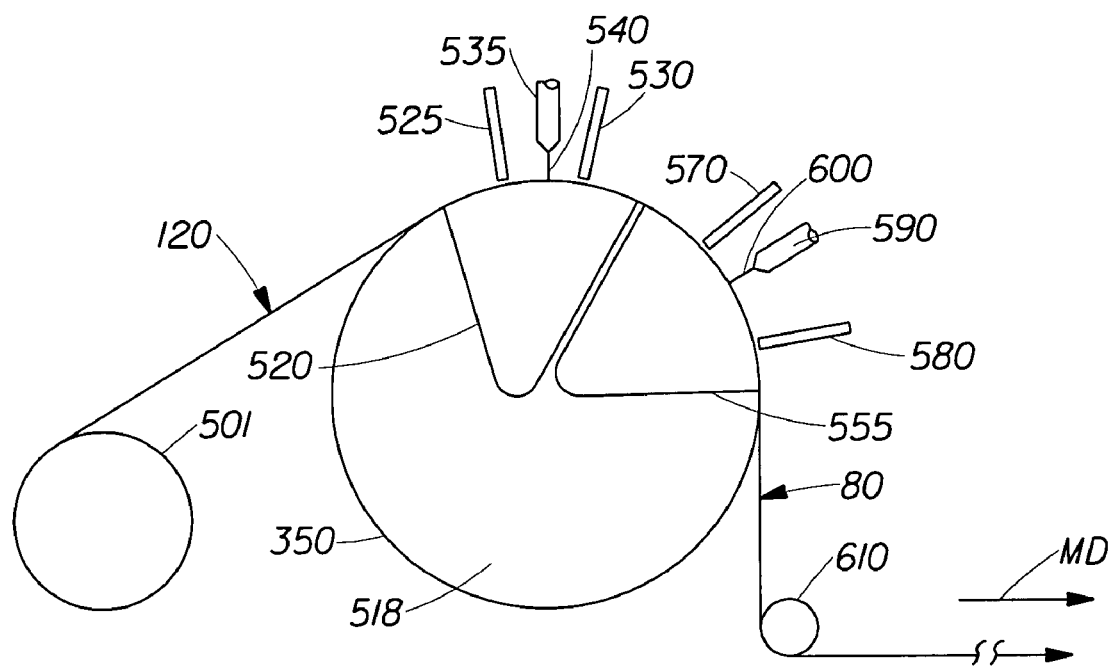
FIG. 9 is a simplified schematic illustration of a single phase forming process of the present invention.

In FIG. 9 there is shown single-phase web process for debossing and drying (if necessary) a continuous polymeric web 80 of the present invention. By single-phase is meant that the process uses only one three-dimensional forming structure. By continuous is meant to distinguish the described process from a batch process in which individual, discrete samples of web are made, often referred to as hand sheets. While it is recognized that webs of the present invention can be batch-processed using the structures described for the continuous process, a continuous process is the preferred method for commercially making a polymeric web of the present invention. Further, while the process described with respect to FIG. 9 is primarily designed to form macroscopically-expanded webs having hair-like fibrils 225 and primary apertures, e.g., apertures 71 of web 80, it is believed that a hydroforming process can be utilized to form a web having only hair-like fibrils by suitably modifying the forming structure to have only protrusions 2250.

Polymeric web 80 of the present invention can be formed by a hydroforming process on a single three-dimensional forming structure 350 and can also be annealed and/or dried on the forming structure 350 prior to rewinding the web into roll stock for further processing. The three-dimensional structures of a polymeric web, e.g., polymeric web 80 shown in FIG. 4, are formed by forcing the web to conform to the forming structure 350, which rotates about stationary forming drum 518. Forming structure 350 is described more fully below, but, in general, it is a three-dimensional form to which the precursor web 120 is forced to conform.

Precursor web 120 can be extruded and chilled immediately prior to being fed directly onto the surface of forming structure 350, or it can be fed from a supply roll, as shown by supply roll 501 in FIG. 9. In some embodiments it is preferred that the temperature of the precursor web 120 be elevated sufficiently to soften it and make it more conformable to the forming structure 350. The temperature of precursor web 120 can be elevated by applying hot air or steam to the web or by passing the web through heated nip rolls, prior to subjecting it to the forming process.

In the process described in FIG. 9, precursor web 120 is fed in a substantially planar condition in the machine direction (MD) from a supply roll 501 onto the surface of forming structure 350. Forming structure 350 rotates at a speed such that the tangential surface velocity of the forming structure 350 substantially matches that of the linear velocity of precursor web 120 in the machine direction, so that during the hydroforming process the web is substantially stationary relative to forming structure 350.

Once precursor web 120 is adjacent to and being "carried on", so to speak, the forming structure 350, precursor web 120 is directed over stationary vacuum chamber 520 which is interior to forming drum 518. Although the hydroforming process described herein can be accomplished to some degree without vacuum chambers, in general, vacuum chambers aid in better three-dimensional web formation as well as liquid removal. As precursor web 120 passes over vacuum chamber 520, the outwardly-exposed surface of precursor web 120 is impinged upon by a liquid jet 540 discharged from high pressure liquid jet nozzle 535 between a pair of stationary liquid baffles 525 and 530 which served to help localize splashing liquid. The effect of the liquid jet 540 is to cause the precursor web to conform to forming structure 350. As precursor web conforms to forming structure 350, both the hair-like fibrils 225 and the primary apertures 71 can be formed. As primary apertures 71 form, vacuum from vacuum chamber 520 aids in removing excess liquid from the web, and, in some cases aids in forming precursor web 120 to forming structure 350. As precursor web 120 is passed under the influence of high pressure liquid jet 540, it is permanently deformed to conform to the forming structure 350, thereby being formed into three-dimensional, macroscopically-expanded polymeric web 80 of the present invention.

In the process described with reference to FIG. 9, a single liquid jet 540 is described as forming both the hair-like fibrils 225 and the primary apertures 71. In another embodiment, additional liquid (or fluid) jets can be used to form the three-dimensional web structures in multiple stages. For example, a first fluid, such as water, can impinge precursor web 120 to form macroapertures 71 in a first stage, and following the first stage, a second fluid, such as hot water or air (optionally in combination with a vacuum chamber) can impinge the partially-formed web to further form the hair-like fibrils 225 in a second stage.

In the process described in FIG. 9, liquid jets 540 and/or drying means 590 can be replaced by re-heat means. Re-heat means refers to means for directing streams of heated gases, such as air, such that the heated air, alone or in combination with vacuum from vacuum chambers 520 or 555, is sufficient to cause precursor web 120 to conform to forming structure 350. Re-heat means are known in the art, for example as disclosed in U.S. Pat. No. 4,806,303 issued to Bianco et al. In general, a re-heat means comprises an air blower and a heater as well as a nozzle to direct forced, heated air onto the surface of a web. In one embodiment the air exiting the nozzle can be between 220 and 305 degrees centigrade and the precursor web 120 can be moved under or across the heated air stream at about 25 meters per minute. In one embodiment vacuum can be maintained at about 365 mm Hg. In embodiments where re-heat means replaces liquid jets 540, drying means 590 are not necessary, but can be utilized if desired, for example as annealing means or further forming means.

Without being bound by theory, it is believed that by adjusting the precursor web properties, the vacuum dwell time, i.e., the time precursor web is adjacent vacuum chambers 520 and/or 555, and/or the level of vacuum, i.e., partial pressure, it is possible to form web 80 on the apparatus shown in FIG. 9 in a cast process without using any liquid jets 540. That is, by suitably adjusting the precursor web properties, e.g., thickness, material, temperature, vacuum alone is sufficient to form a web 80 that conforms to forming structure 350. In a cast process precursor web 120 is extruded directly onto the surface of forming structure 350 such that web 80 formation can occur prior to cooling of precursor web 120.

In general, therefore, one fluid (e.g., water or air) or more than one fluid (e.g., water, air) can be directed to impinge on, and do energetic work on, precursor web 120 in one or more stages. It is believed that, for thermoplastic precursor webs 120, as the temperature of the precursor web approaches its melting point, it more easily stretches without rupture to form over protrusions 2250 of forming structure 350. However, for forming macroapertures it is more desirable to have relatively high strain rates and relatively rapid rupture, and for forming hair-like fibrils it is more desirable to have relatively low strain rates and no rupture. Accordingly, in a two-stage forming process, the temperature of the impinging fluid at first and/or second stages can be adjusted independently, depending on the dwell time over which each impingement acts and the temperature of the precursor web 120 to form both macroapertures 71 and high aspect ratio hair-like fibrils 225 independently.

For making webs suitable for use as a topsheet in a disposable absorbent article, precursor web 120 can be a polyolefinic film from about 10 microns to about 100 microns in total thickness. For such precursor webs 120, high pressure liquid jet 540 is typically water at a temperature from about 15-95 degrees C., operated at a pressure in the range of about 200 psig to about 1200 psig and a water flow rate in the range of about 18 liters (4 gallons) per minute to about 62 liters (14 gallons) per minute per 25.4 cross-machine direction (CD) mm (1 inch) of width of the precursor web 120.

After passing beyond the high pressure liquid jet 540, (or jets, as discussed above), polymeric web 80 of the present invention can be dried while still on forming structure 350. For example, as shown in FIG. 9, polymeric web 80 can be directed, while still on forming structure 350, under the influence of drying means 590. Drying means 590 can be any of means for removing, or driving off liquids from polymeric webs, such as radiant heat drying, convective drying, ultrasonic drying, high velocity air knife drying, and the like. In general, a drying medium 600 can be utilized, such as heated air, ultrasonic waves, and the like. A stationary vacuum chamber 555 can be utilized to aid in drying by means of a partial pressure inside forming drum 518. Drying means 590 can be designed to drive liquid off of polymeric web 80 and into vacuum chamber 555. Baffles 570 and 580 can be utilized to locally contain any liquid that gets removed and does not enter vacuum chamber 555. Baffles 570 and 580 can also serve to localize and direct heat or heated air used for drying.

Using a heated drying medium 600 has an additional benefit for making webs 80 of the present invention. Prior art macroscopically-expanded, three-dimensional polymeric webs, such as the webs disclosed in the aforementioned Curro '643, are dried in a separate process after being removed form their respective forming structures. These webs are typically wound onto a roll for storage until needed for web processing of disposable articles, for example. One problem associated with prior art webs is the compression setting that occurs during winding and storage. Without being bound by theory, it is believed that three-dimensional polyethylene webs can experience a secondary crystallization over time which "locks in" the collapsed, wound state of the web. It has been found that by first annealing three-dimensional polymeric webs by subjecting them to elevated temperatures for a sufficient time, this observed compression set is reduced or prevented altogether. In general, however, it is difficult to subject prior art webs to the requisite temperatures due to the relatively fragile structure. That is, if a prior art web is subjected to annealing temperatures, the web tends to lose the three-dimensional structure formed on the forming structure. For this reason, therefore, drying the web while still on the forming structure provides a significant processing benefit by permitting processing with sufficiently high annealing temperatures to anneal the web, while at the same time drying it. The annealing temperature will vary depending on the time of drying, the polymer used and the thickness of the web, but, in general, for polyolefinic webs, a drying/annealing temperature of between about 50-250 degrees C. is sufficient.

After polymeric web 80 passes the drying (or drying/annealing) stage of the process it can be removed from the forming structure 350 about roller 610 and is thereafter rewound or fed directly to subsequent converting operations.

A forming structure of the present invention, such as forming structure 350 referred to with respect to FIG. 9, is necessary for making a web of the present invention. The forming structure is sometimes referred to as a forming screen. FIG. 10 shows a portion of a forming structure of the present invention 350 in partial perspective view. The forming structure 350 exhibits a plurality of forming structure apertures 710 defined by forming structure interconnecting members 910. Forming structure apertures 710 permit fluid communication between opposing surfaces, that is, between forming structure first surface 900 in the plane of the first surface 1020 and forming structure second surface 850 in the plane of the second surface 1060. Forming structure sidewall portions 830 extend generally between the forming structure first surface 900 and forming structure second surface 850. Protrusions 2200 extend from forming structure first surface 900 to form generally columnar, pillar-like forms.

A comparison of FIG. 10 with FIG. 3 shows the general correspondence of forming structure 350 with polymeric web 80 of the present invention. That is, the three-dimensional protrusions 2250 and depressions (e.g., apertures 710) of forming structure 350 have a one-to-one correspondence to the hair-like fibrils 225 and primary apertures 71, respectively, of polymeric web 80. The one-to-one correspondence is necessary to the extent that the forming structure 350 determines the overall dimensions of the polymeric web 80 of the present invention. However, the distance between plane of the first surface 102 and plane of the second surface 106 of the polymeric web 80 need not be the same as the distance between the plane of the first surface 1020 and the plane of the second surface 1060 of forming structure 350. This is because the distance "T" for polymeric web 80, as shown in FIG. 5, is not dependent upon the actual thickness of forming structure 350, the thickness being the perpendicular distance between the plane of the first surface 1020 and the plane of the second surface 1060 of forming structure 350.

FIG. 11 is a further enlarged, partial perspective view of the forming structure 350 shown in FIG. 10, and compares with the similar view of polymeric web 80 in FIG. 4. Protrusions 2250 can be made by methods described below to extend from first surface 900 to a distal end 2260. As shown in the further enlarged view of FIG. 12, protrusions 2250 can have a height hp measured from a minimum amplitude measured from first surface 900 between adjacent protrusions to distal end 2260. Protrusion height hp can be at least about 50 microns (about 0.002 inch) and can be at least about 76 microns (about 0.003 inch), and can be at least about 152 microns (about 0.006 inch), and can be at least about 250 microns (about 0.010 inch), and can be at least about 381 microns (about 0.015 inch). Protrusions 2250 have a diameter dp, which for a generally cylindrical structure is the outside diameter. For non-uniform cross-sections, and/or non-cylindrical structures of protrusions 2250, diameter dp is measured as the average cross-sectional dimension of protrusions at ½ the height hp of the protrusions 2250, as shown in FIG. 12. Protrusion diameter dp can be about 50 microns (about 0.002 inch), and can be at least about 66 microns, and can be about 76 microns (about 0.003 inch), and can be at least about 127 microns (about 0.005 inch). Thus, for each protrusion 2250, a protrusion aspect ratio, defined as hp/dp, can be determined. Protrusions 2250 can have an aspect ratio hp/dp of at least 1, and as high as 3 or more. The aspect ratio can be at least about 5 and can be about 6. In one embodiment, protrusions had a substantially uniform diameter of about 66 microns over a height of about 105 microns, for an aspect ratio of about 1.6. The protrusions 2250 can have a center-to-center spacing Cp between two adjacent protrusions 2250 of between about 100 microns (about 0.004 inch) to about 250 microns (about 0.010 inch). In one embodiment the center-to-center spacing was 179 microns. In general, it is believed that the actual distance between two adjacent protrusions 2250 (i.e., a "side-to-side" dimension) should be greater than twice the thickness t of precursor web 120 to ensure adequate deformation of precursor web 120 between adjacent protrusions 2250.

In general, because the actual height hp of each individual protrusion 2250 may vary, an average height $hp_{avg}$ of a plurality of protrusions 2250 can be determined by determining a protrusion average minimum amplitude $Ap_{min}$ and a protrusion average maximum amplitude $Ap_{max}$ over a predetermined area of forming structure 350. Likewise, for varying cross-sectional dimensions, an average protrusion diameter $dp_{avg}$ can be determined for a plurality of protrusions 2250. Such amplitude and other dimensional measurements can be made by any method known in the art, such as by computer aided scanning microscopy and related data processing. Therefore, an average aspect ratio of the protrusions 2250, $ARp_{avg}$ for a predetermined portion of the forming structure 350 can be expressed as $hp_{avg}/dp_{avg}$. The dimensions hp and dp for protrusions 2250 can be indirectly determined based on the known specifications for making forming structure 350, as disclosed more fully below.

In one embodiment the diameter of protrusions 2250 is constant or decreases with increasing amplitude. As shown in FIG. 12, for example, the diameter, or largest lateral cross-sectional dimension, of protrusions 2250 is a maximum near first surface 900 and steadily decreases to distal end 2260. This structure is believed to be necessary to ensure that the polymeric web 80 can be readily removed from the forming structure 350.

Forming structure 350 can be made of any material that can be formed to have protrusions 2250 having the necessary dimensions to make a web of the present invention, is dimensionally stable over process temperature ranges experienced by forming structure 350, has a tensile modulus of at least about 5 MPa, more preferably at least about 10M Pa, more preferably at least about 30 MPa more preferably at least about 100-200 MPa, and more preferably at least about 400 MPa, a yield strength of at least about 2 MPa, more preferably at least about 5 MPa more preferably at least about 10 MPa, more preferably at least about 15 MPa, and a strain at break of at least about 1%, preferably at least about 5%, more preferably at least about 10%. It has been found that relatively tall, high aspect ratio protrusions form better webs as the modulus of the material of the forming structure increases, as long as it has sufficient strain at break (i.e., not too brittle) so as not to break. For modulus and yield strength data, values can be determined by testing according to known methods, and can be tested at standard TAPPI conditions at a strain rate of 100%/minute.

Dimensional stability with respect to thermal expansion is necessary only for commercial processes as described with respect to FIG. 9, because for some process conditions the forming structure 350/forming drum 518 interface can be compromised if the forming structure 350 expands or contracts more than the forming drum 518. For batch processing of polymeric webs of the present invention dimensional stability is not a requirement. However, for all commercial processes it is necessary that the forming structure be made of a material suitable for the processing temperature ranges. Process temperature ranges are affected by process conditions including the temperature of the fluid jet, e.g., liquid jet 540, and the temperature of forming structure 350, which can be heated, for example. In general, for polyolefinic webs, including laminated, co-extruded films for use in webs for disposable absorbent articles (i.e., films having a thickness, t, of about 10-100 microns), a water temperature of between 15 degrees C. and 95 degrees C. can be used. The drying/annealing air temperature can be 250 degrees C. or less. In general, process temperatures can be varied throughout a wide range and still make the polymeric web 80 of the present invention. However, the temperature ranges can be varied to make polymeric web 80 at optimal rates depending on film thickness, film type, and line speed.

In a preferred embodiment, protrusions 2250 are made integrally with forming structure 350. That is, the forming structure is made as an integrated structure, either by removing material or by building up material. For example, forming structure 350 having the required relatively small scale protrusions 2250 can be made by local selective removal of material, such as by chemical etching, mechanical etching, or by ablating by use of high-energy sources such as electrical-discharge machines (EDM) or lasers.

Acid etching of steel structures as disclosed in the aforementioned Ahr '045 patent, is believed to be only capable of making protrusions having an aspect ratio of 1 or less. Without being bound by theory it is believed that acid etching steel in small, incremental steps may be result in the high aspect ratios preferred in a forming structure of the present invention, but it is expected that the resulting protrusion(s) would be severely undercut to have "mushroom" shaped profiles. It is not currently known by the inventors of the present invention how one might acid etch steel as taught in Ahr '045 to form the generally cylindrical protrusions 2250 of the present invention having the requisite aspect ratio. Likewise, forming protrusions on steel by electroplating is believed to result in "mushroom" shaped protrusions. In both instances, i.e., acid etching and electroplating, the mushroom shape is expected due to the nature of the material removal/deposition. Material would not be removed/deposited only in a general aligned, e.g., vertical manner. Therefore, it is currently known to make metal forming structures 350 only by use of electrical-discharge machines (EDM) or lasers.

Figure 13:
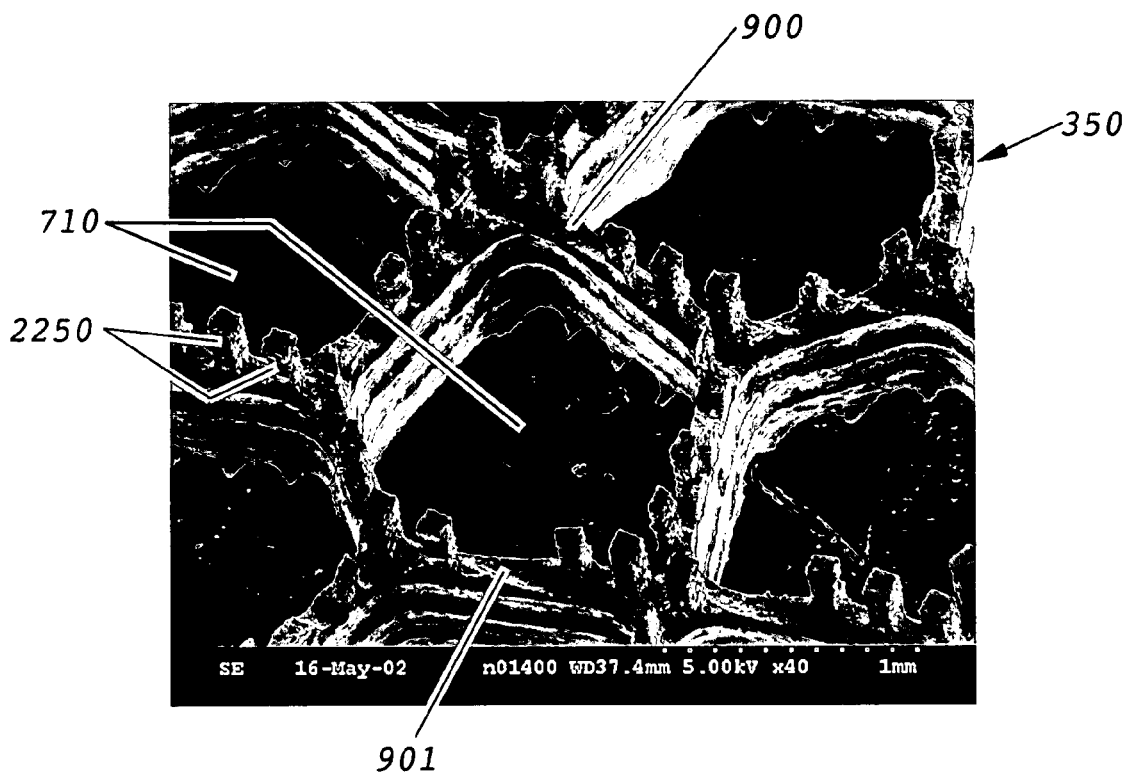
FIG. 13 is a photomicrograph of one embodiment of a forming structure of the present invention.
Figure 14:
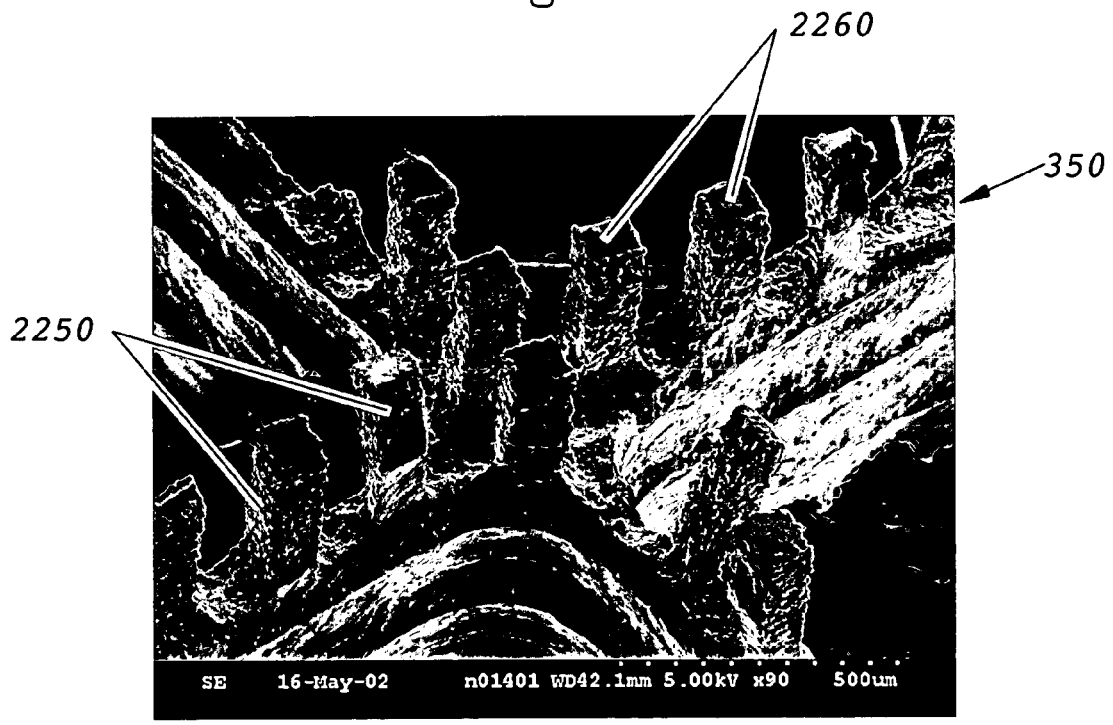
FIG. 14 is an enlarged view of a portion of the forming structure of FIG. 13.

A portion of a prototype forming structure 350 made of steel and having protrusions 2250 made by a conventional EDM process is shown in FIGS. 13 and 14. FIG. 13 is a photomicrograph of a forming structure 350 and FIG. 14 is a further enlarged view the forming structure of FIG. 13. As shown in FIG. 13, a steel forming structure has been subjected to an EDM process to form integral protrusions 2250 having distal ends 2260. The forming structure 350 shown in FIGS. 13 and 14 has depressions 710 generally similarly shaped to those shown in FIG. 3. However, as can be seen in FIGS. 13 and 14, the structure is less than ideal for making topsheets for absorbent articles because of the geometrical constraints of both the forming structure 350 prior to the EDM process, and the EDM process itself. Specifically, as can be seen, first surface 900 of forming structure interconnecting members 910 is only one protrusion "wide". Also, as can be seen in FIG. 13, due to the geometrical constraints of the process of EDM, gaps between protrusions 2250 can result. For example, gap 901 in FIG. 13 resulted from the EDM wire being oriented slightly off parallel from the respective forming structure interconnecting members 910 shown. Therefore, for commercially successful production of webs suitable for topsheets in disposable absorbent articles, the forming structure shown in FIG. 13 may not be acceptable. However, it is clear that suitably shaped protrusions 2250 having the required aspect ratios can be formed. The protrusions 2250 of the forming structure shown in FIG. 13 have an average height $hp_{avg}$ of about 275 microns (0.011 inch), and an average diameter of about $dp_{avg}$ of about 100 microns (0.004 inch), defining an average aspect ratio of $ARp_{avg}$ of about 2.7. (Note that the forming screen shown in FIGS. 13 and 14 is a prototype, and has been processed by EDM on both sides. In practice, it is only necessary to form protrusions on one side.)

In another method of making forming structure 350, a base material susceptible to laser modification is laser "etched" to selectively remove material to form protrusions 2250 and forming structure apertures 710. By "susceptible to laser modification" means that the material can be selectively removed by laser light in a controlled manner, recognizing that the wavelength of light used in the laser process, as well as the power level, may need to be matched to the material (or vice-versa) for optimum results. Currently known materials susceptible to laser modification include thermoplastics such as polypropylene, acetal resins such as DELRIN® from DuPont, Wilmington DE, USA, thermosets such as crosslinked polyesters, or epoxies, or even metals such as aluminum or stainless steel.

In one embodiment a forming structure can be laser machined in a continuous process. For example, a polymeric material such as DELRIN® can be provided in a cylindrical form as a base material having a central longitudinal axis, an outer surface, and an inner surface, the outer surface and inner surface defining a thickness of the base material. A moveable laser source can be directed generally orthogonal to the outer surface. The moveable laser source can be moveable in a direction parallel to the central longitudinal axis of the base material. The cylindrical base material can be rotated about the central longitudinal axis while the laser source machines, or etches, the outer surface of the base material to remove selected portions of the base material in a pattern that defines a plurality of protrusions. Each protrusion can be the generally columnar and pillar-like protrusions 2250, as disclosed herein. By moving the laser source parallel to the longitudinal axis of the cylindrical base material as the cylindrical base material rotates, the relative movements, i.e., rotation and laser movement, can be synchronized such that upon each complete rotation of cylindrical base material a predetermined pattern of protrusions can be formed in a continuous process similar to "threads" of a screw.

Figure 15:
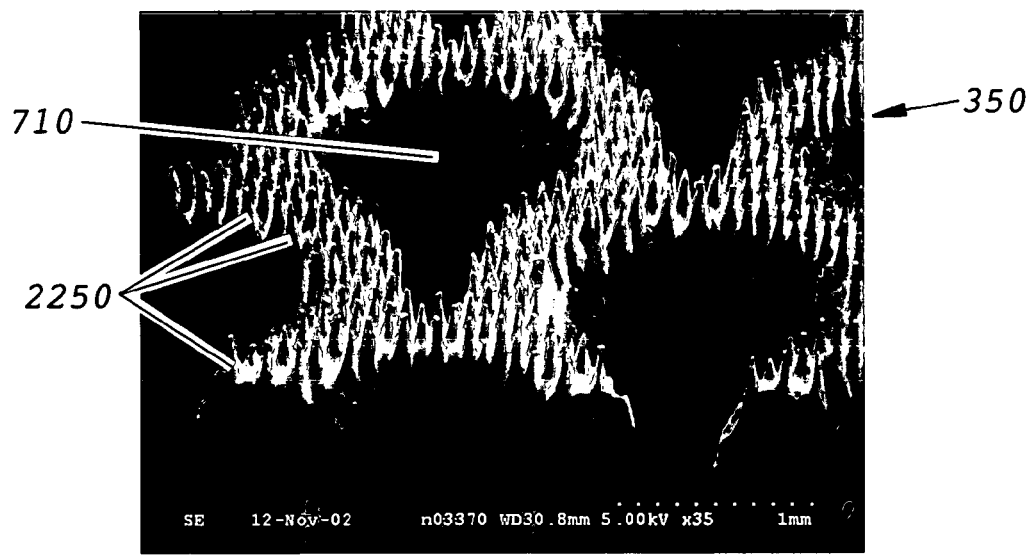
FIG. 15 is a photomicrograph of another embodiment of a forming structure of the present invention.
Figure 16:
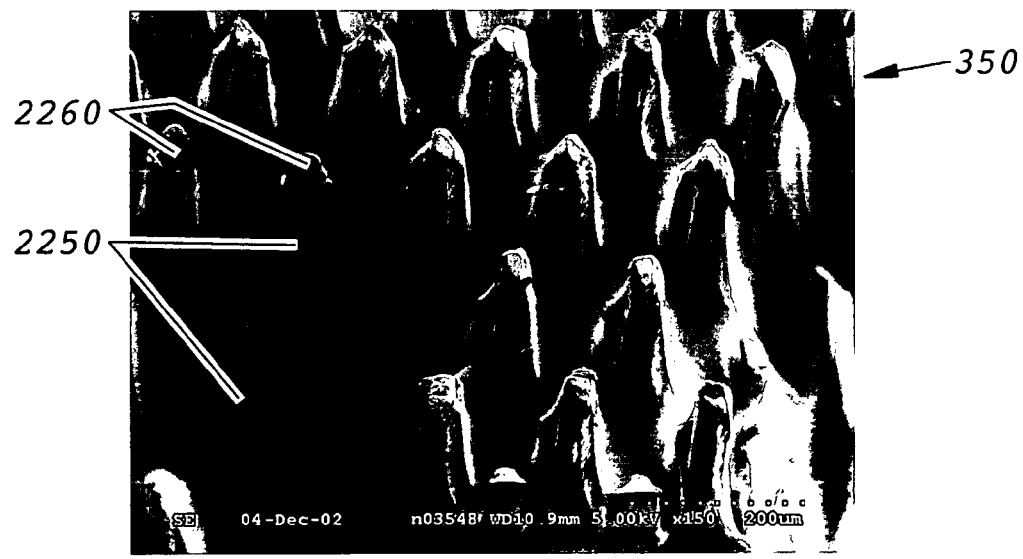
FIG. 16 is an enlarged view of a portion of a forming structure similar to that shown in FIG. 15.

FIG. 15 is a photomicrograph of laser-etched embodiment of a forming structure 350 of the present invention. FIG. 16 is an enlarged view of another, but similar, forming structure 350 of the present invention. The forming structures 350 shown in FIGS. 15 and 16 are made by first forming a polymer layer having formed therein depressions 710, which as shown are generally "teardrop" shaped and would make generally teardrop shaped primary apertures 71 in web 80 of the present invention. The depressions 710 can be formed, for example, by laser etching the depressions first. The polymer layer having depressions 710 therein can also be formed by radiating a liquid photosensitive resin such as a UV-light-curable polymer, through an appropriate masking layer on an underlying support layer (not shown) such as a foraminous woven backing. Suitable polymer layers, support layers, masking layers and UV-curing processes are well known in the art of making paper-making belts and are disclosed in U.S. Pat. No. 5,334,289 issued to Trokhan et al., on Aug. 2, 1994; and U.S. Pat. No. 4,529,480 issued to Trokhan on Jul. 16, 1985; and U.S. Pat. No. 6,010,598 issued to Boutilier et al. on Jan. 4, 2000, each of these patents, being hereby incorporated herein by reference for the teaching of structures, resins and curing techniques. As disclosed in the Boutilier '598 patent, for example, one suitable liquid photosensitive resin composition is comprised of four components: a prepolymer; monomers; photoinitiator and antioxidants. A preferred liquid photosensitive resin is Merigraph L-055 available from MacDermid Imaging Technology, Inc. of Wilmington, Del.

After the polymer layer is cured to have depressions 710 the polymer layer is laser etched to form protrusions 2250 having distal ends 2260. Laser etching can be achieved by known laser techniques, selecting wavelength, power, and time parameters as necessary to produce the desired protrusion dimensions. In the forming structure of FIG. 16, protrusions have an average height hp of 250 microns and an average diameter dp of 85 microns (at ½ height hp) and an aspect ratio arp of about 2.9.

In one embodiment, forming structure 350 formed as a cured polymer on a support layer can be used as is, with the support layer being a part of forming structure 350. However, in another embodiment, the cured polymer can be removed from the support layer and used alone. In this case, it may be desirable to only partially cure the polymer, remove the support layer 903 and finish fully curing the polymer material.

Figure 17:
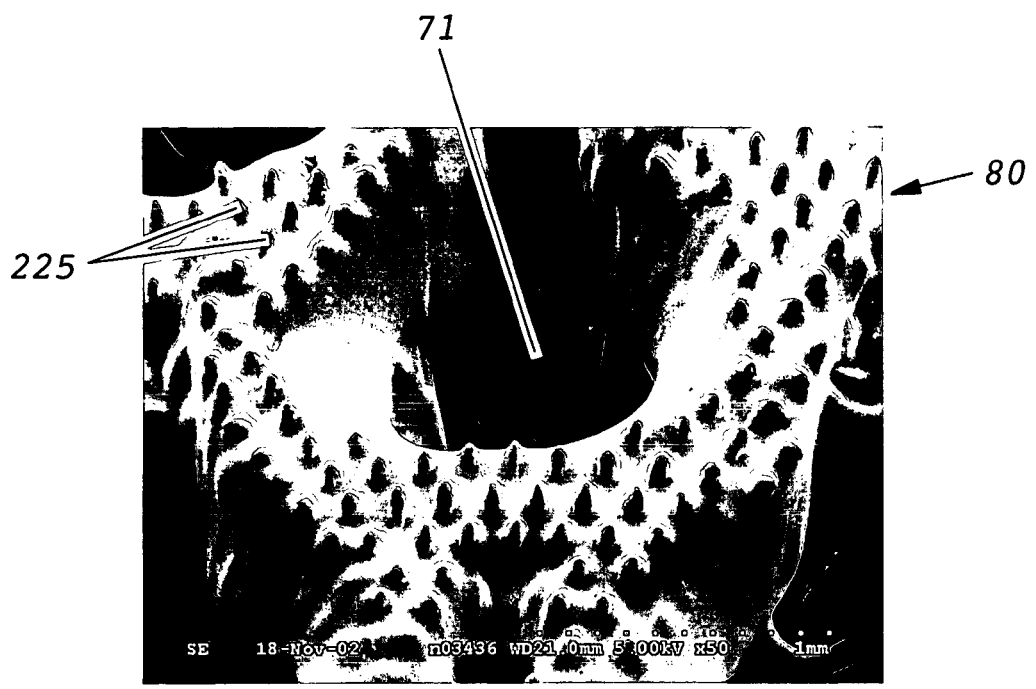
FIG. 17 is a photomicrograph of a portion of a web made on a forming structure of the present invention.
Figure 18:
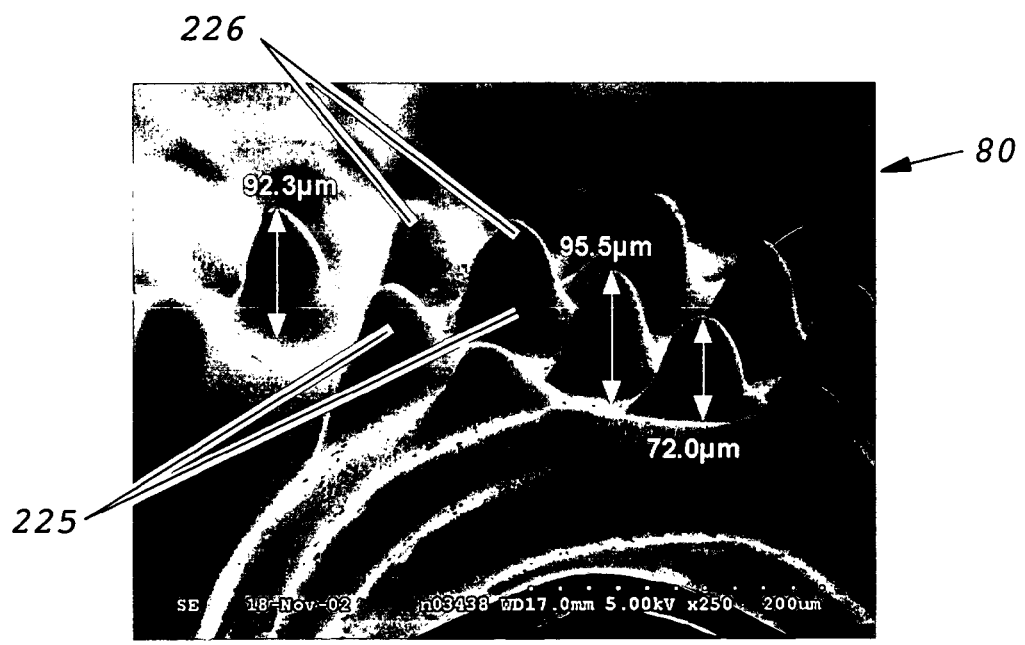
FIG. 18 is an enlarged view of a portion of the web shown in FIG. 17.

A web 80 made on the forming structure shown in FIG. 15 is shown in the photomicrographs of FIGS. 17 and 18. FIG. 17 is a photomicrograph of a portion of web 80 showing hair-like fibrils 225 and aperture 71. FIG. 18 is a further enlarged view of web 80 showing in more detail hair-like fibrils 225 having closed distal ends 226. The precursor web 120 for the web 80 shown in FIGS. 17 and 18 was made from a 25 micron (0.001 inch) thick Dowlex 2045A precursor film 120.

Figure 19:
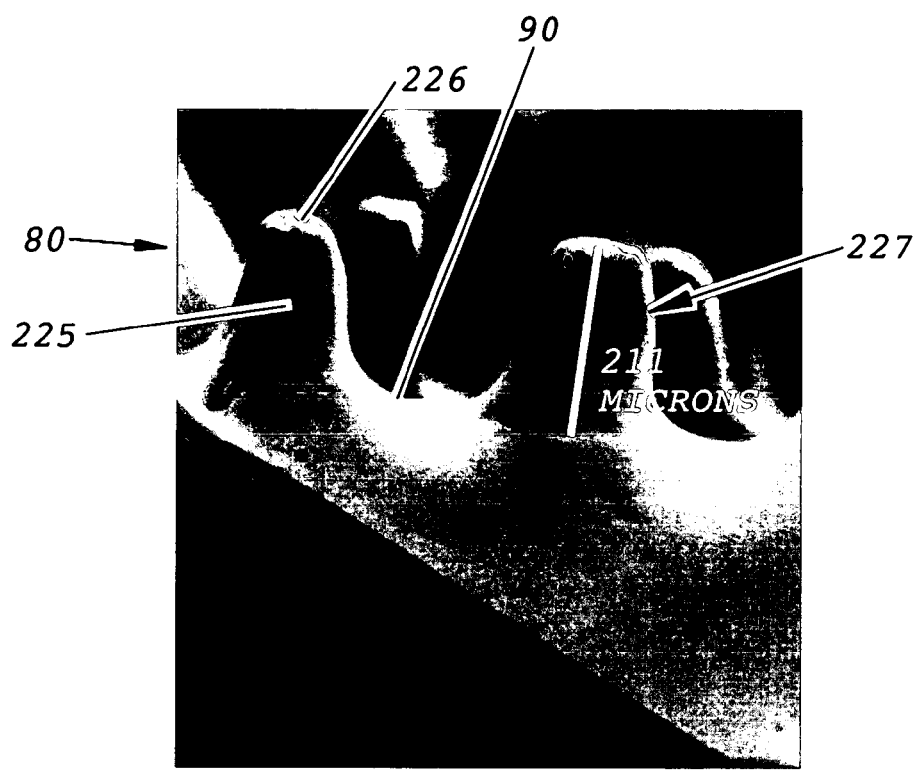
FIG. 19 is a photomicrograph of a portion of a web made on a forming structure of the present invention.
Figure 20:
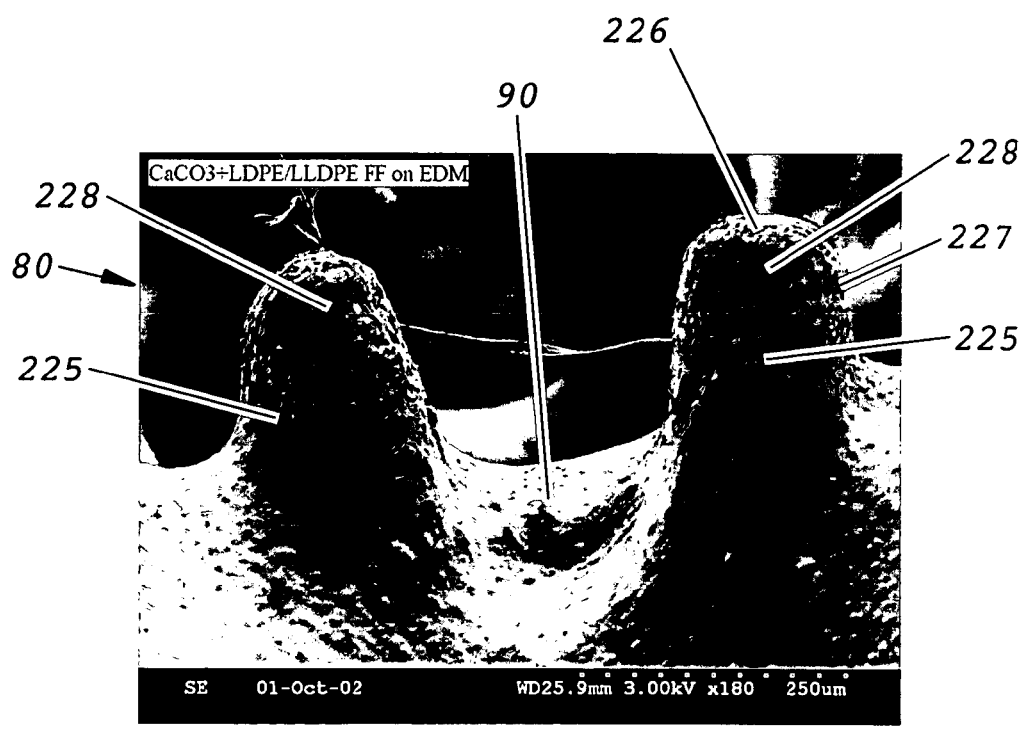
FIG. 20 is an enlarged view of a portion of a web made on a forming structure of the present invention.

FIGS. 19 and 20 show greatly enlarged portions of webs 80 made in batch processes on the forming structure shown in FIGS. 13 and 14 to more closely show details of hair-like fibrils 225. The polymer webs 80 shown in FIGS. 19 and 20 have primary apertures 71 (not shown) generally in a penta-hexagon shape, each having a projected area in the first surface 90 of about 1.4 square millimeters. The spacing between primary apertures 71 is such that the open area primary apertures 71 as projected in the first surface 90 is up to 65% of total surface area. The web 80 exhibits about 4,650 hair-like fibrils 225 per square centimeter of first surface 90 area (about 30,000 hair-like fibrils 225 per square inch). This concentration of hair-like fibrils 225 is referred to as the "density" or "area density" of hair-like fibrils 225, and represents the number of hair-like fibrils per unit area of first surface 90, as opposed to total area of polymer web 80. Thus, the regions of polymer web 80 corresponding to primary apertures 71 do not contribute to the area when calculating density. In general, the density is determined by the average center-to-center spacing of the protrusions 2250 on forming structure 350, which is about 150 microns (0.006 inch) for the forming structure shown in FIGS. 13 and 14.

It is believed that a polymer web 80 of the present invention suitable for use as a topsheet on a disposable absorbent article (e.g., a sanitary napkin) should have a density of hair-like fibrils 225 of at least about 1550 per square centimeter (about 10,000 per square inch). The density of hair-like fibrils 225 can be about 2325 per square centimeter (about 15,000 per square inch), and can be about 3100 per square centimeter (about 20,000 per square inch) and can be about 3875 per square centimeter (about 25,000 per square inch). Since for some webs it may be difficult to determine exactly where first surface 90 begins and ends, density can be approximated by taking total area of a predetermined portion of polymer web 80 and subtracting out the area of primary apertures 71 as projected in the first surface 90 of that predetermined portion. The area of primary apertures 71 can be based on the projected area of the depressions 710 of forming structure 350. By "projected area" is meant the area of a surface if it were projected onto a plane parallel to that surface, and can be imagined by analogy, for example, as an "ink stamp" of the surface.

FIG. 19 is a photomicrograph of a web 80 made from a 25 micron (0.001 inch) DOWLEX® 2045A precursor film 120. As shown, the web 80 of FIG. 19 comprises discrete hair-like fibrils 225, each of the hair-like fibrils 225 being a protruded extension of first surface 90. Each of the hair-like fibrils 225 has a side wall 227 defining an open portion 229 (as shown in FIG. 5) and a closed distal portion 226. The hair-like fibrils 225 shown have a height of about 211 microns, and a diameter at ½ their height of about 142 microns, resulting in an aspect ratio of about 1.5.

The web 80 of FIG. 20 comprises discrete hair-like fibrils 225, each of the hair-like fibrils 225 being a protruded extension of first surface 90. Each of the hair-like fibrils 225 has a side wall 227 defining an open portion 229 (as shown in FIG. 5) and a closed distal portion 226. The hair-like fibrils 225 shown in FIG. 20 have an aspect ratio AR of at least 1.

The difference between the webs 80 shown in FIGS. 19 and 20 is that the precursor film 120 used to make the polymeric web 80 shown in FIG. 20 was a coextruded four layer polyethylene film comprising calcium carbonate in one of the outermost layers. Specifically, the calcium carbonate was added into the polymer melt for the polymer that forms the first surface of web 80 after formation of hair-like fibrils 225. The four layers comprised polyethylene in the follow order: (1) ExxonMobil NTX-137 at about 42 volume percent; (2) ExxonMobil Exact 4151 at about 16 volume percent; (3) ExxonMobil Exact 4049 at about 32 volume percent; and (4) a mixture of 57 weight percent Ampacet 10847 with calcium carbonate blended in as a master batch and 43 weight percent ExxonMobil LD 129, this mixture at a volume percent of about 10 percent. The precursor film 120 had a starting thickness of about 25 microns (0.001 inch).

One interesting and unexpected result of using a $CaCO_3$/PE blend for a skin layer of precursor film 120 is the formation of regions of roughened outer surfaces 228 at or near the distal end 226 of hair-like fibrils 225 as can be seen on the web shown in FIG. 20. These regions of relatively greater surface roughness 228, which have less surface smoothness than the surrounding surfaces, such as first surface 90, provide for a more cloth-like appearance due to its inherent low gloss, and an even greater soft and silky tactile impression. Without being bound by theory, it is believed that the relatively roughened surface texture of the distal ends of hair-like fibrils 225 gives greater texture that is experienced as softness to the skin of a person touching the surface. Without being bound by theory, it is believed that the formation of roughened outer surfaces at or near the distal end 226 of hair-like fibrils 225 is a result of deep drawing precursor web having therein particulate matter. It appears that possibly the particulate matter, in this case $CaCO_3$, causes stress concentrations in the film blend that give rise to surface discontinuities. At the points of maximum strain, i.e., at the point of maximum draw of hair-like fibrils 225, the surface of the film (i.e., precursor film 120) breaks up, exposing particulate matter on the surface of the hair-like fibrils 225.

Therefore, in one embodiment polymer web 80 can be described as having hair-like fibrils 225 in which at least a portion near the distal end 226 thereof exhibits regions of relatively greater surface roughness 228 than the remaining portions. By using different additive particulate matter, the regions of relatively greater surface roughness 228 can provide for other benefits. For example, particulate skin treatments or protectants or odor-absorbing actives can be used. Importantly, webs 80 comprising particulate matter permit actives to be delivered to the skin of a wearer of an article using web 80 in a very direct and efficient manner.

In general, it is believed that any non-diffusing ingredient (particulate and non-particulate) blended into the melt of a polymer of precursor web 120 can be exposed upon strain of the polymer near the distal end of hair-like fibrils 225. Specifically, actives such as skin care agents can be localized substantially at or near distal ends 226 which can be the primary skin contact surfaces for web 80. Other known methods of imparting localized strain to polymeric films can also serve to expose non-diffusing ingredients in layers. For example, embossing, ring rolling, thermovacuum forming, and other known processes can provide for localized rupture and exposure of active ingredients of polymer films.

Other methods of making forming structure 350 include building up the structure by way of localized electroplating, 3-D deposition processes, or photoresist techniques. One 3-D deposition process is a sintering process. Sintering is similar to stereo lithography in which layers of powdered metal are built up to produce a final work piece. However, it is believed that sintering processes may be limited in resolution. Photoresist techniques include forming a three dimensional structure by use of an appropriate mask over a liquid photosensitive resin, such as the UV-curable polymer disclosed above. UV curing is effective at curing only the portions of a liquid resin exposed to UV light from a UV light source. The remaining (uncured) portions of the liquid resin can then be washed off, leaving behind only the cured portions. The liquid resin UV-curable polymer can be placed on a tray, for example, to a desired depth or thickness and appropriately masked and UV light-cured to selectively cure the portions to be protrusions 2250 and to not cure the portions that will be the apertures 710.

Figure 21:
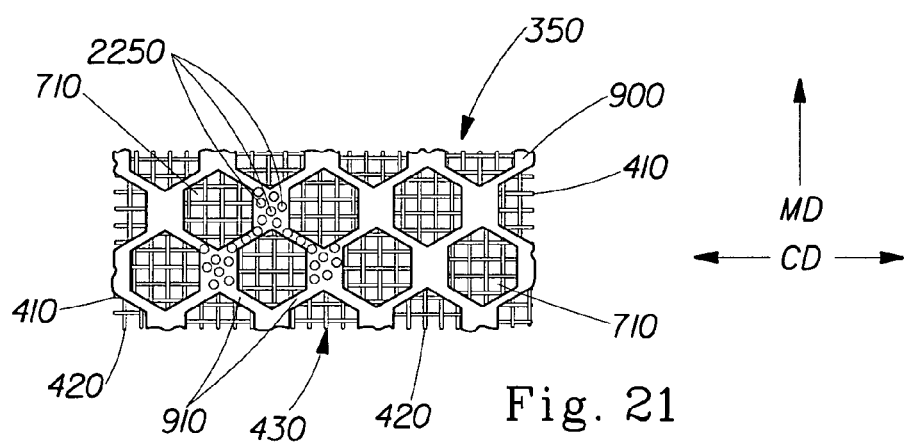
FIG. 21 is a plan view of a forming structure of the present invention.
Figure 22:
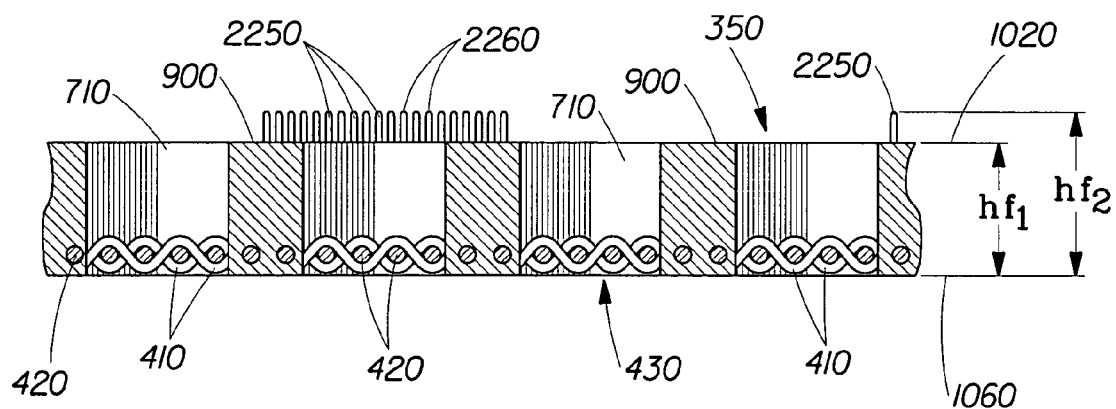
FIG. 22 is a cross-sectional view of the forming structure shown in FIG. 21.

In another embodiment, a flexible polymeric forming structure 350 as shown in FIGS. 21 and 22 can be formed from the polymerization of a UV-curable polymer on an air-permeable backing screen 430. First surface 900 defines apertures 710 which, in the illustrated embodiment are hexagons in a bilaterally staggered array. It is to be understood that, as before, a variety of shapes and orientations of apertures 710 can be used. FIG. 22 illustrates a cross sectional view of that portion of forming structure 350 shown in FIG. 28 as taken along line 22-22. Machine direction reinforcing strands 420 and cross direction reinforcing strands 410 are shown in both FIGS. 21 and 22. Together machine direction reinforcing strands 420 and cross direction reinforcing strands 410 combine to form a foraminous woven element 430. One purpose of the reinforcing strands is to strengthen the flexible polymeric forming structure 350. As shown, reinforcing strands 410 and 420 can be round and can be provided as a square weave fabric around which the UV-curable resin has cured. Any convenient filament size in any convenient weave can be used, although, in general, the more open the weave the better. A more open weave generally results in better air flow through the apertures 710. Better air flow results in better, i.e., more economical, hydroforming when forming structure 350 is used to form a polymeric web, such as polymeric web 80. In one embodiment forming structure 350 430 is a metal screen, such as is commonly used on household doors and windows. In one embodiment the metal screen is an 18×16 mesh bright aluminum screening having a filament diameter for both machine direction filaments 420 and cross direction filaments 410 of 0.24 mm, available as Hanover Wire Cloth from Star Brand Screening, Hanover, Pa., USA, having.

Figure 26:
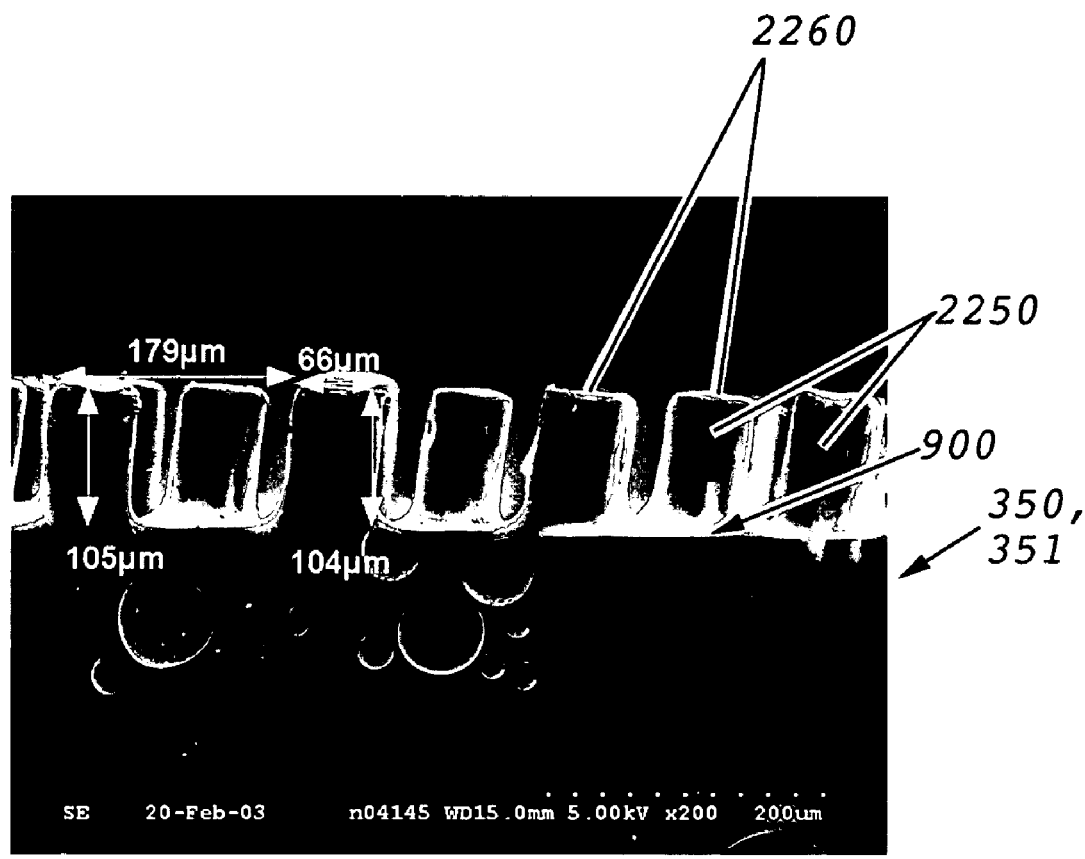
FIG. 26 is a photomicrograph showing in cross section an enlarged portion of the forming structure shown in FIG. 24.

As shown in FIGS. 21 and 22, protrusions 2250 extend from first surface 900 and have distal ends 2260 that are generally rounded in shape. In another embodiment, as shown in the photomicrograph of FIG. 26, the distal ends can be generally flattened into a plateau. The forming structure shown in FIG. 26 is a flexible polymeric forming structure formed by a two-stage process of polymerizing a UV-curable resin.

Figure 23:
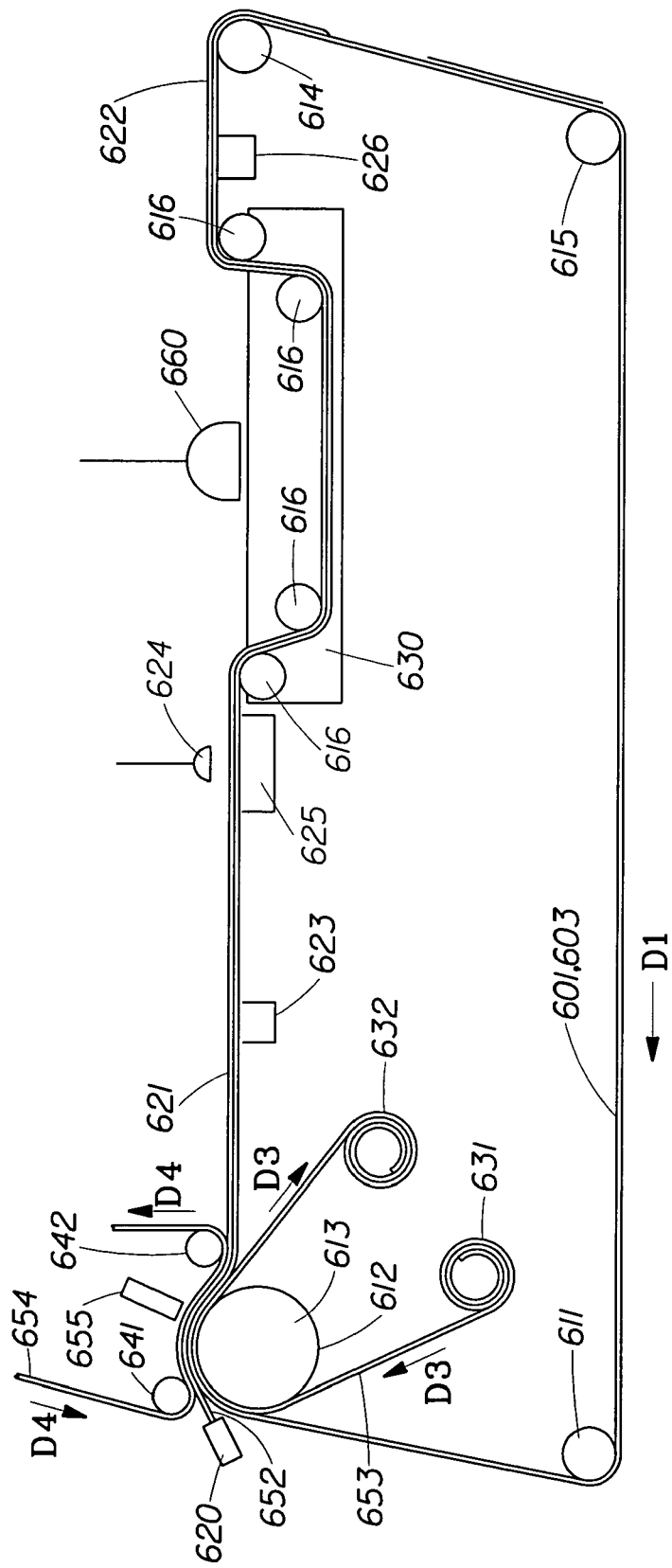
FIG. 23 is a schematic representation of a method from making a forming structure of the present invention.
Figure 24:
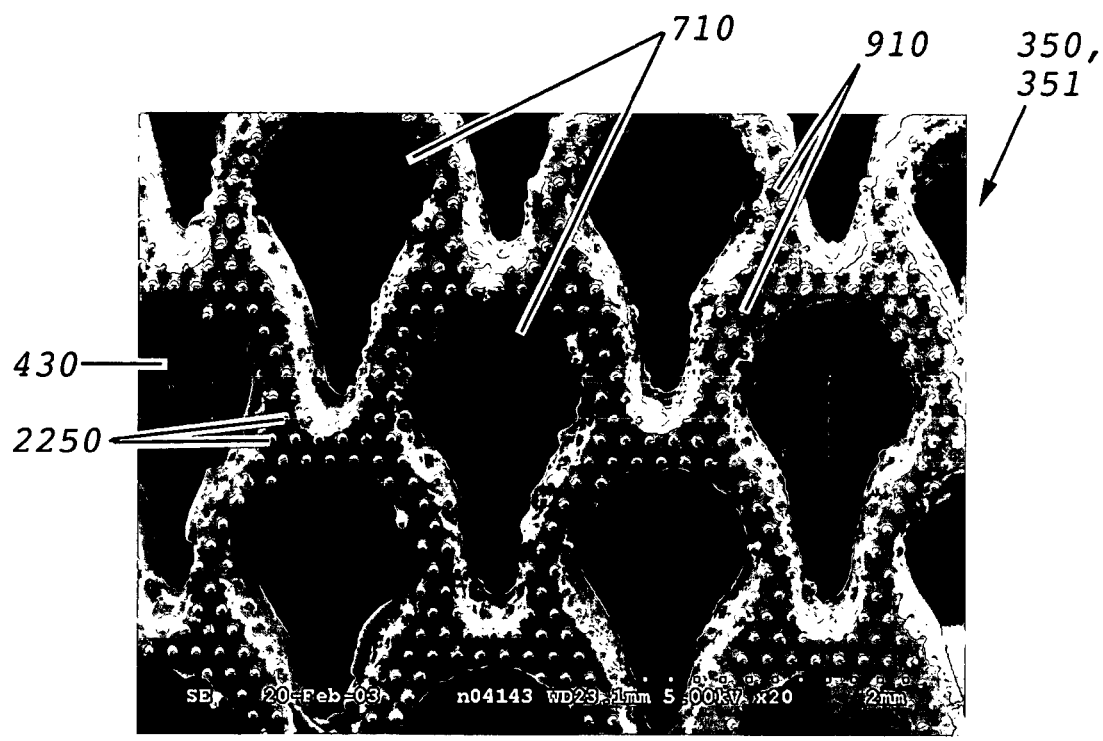
FIG. 24 is a photomicrograph showing an enlarged portion of a forming structure of the present invention.
Figure 25:
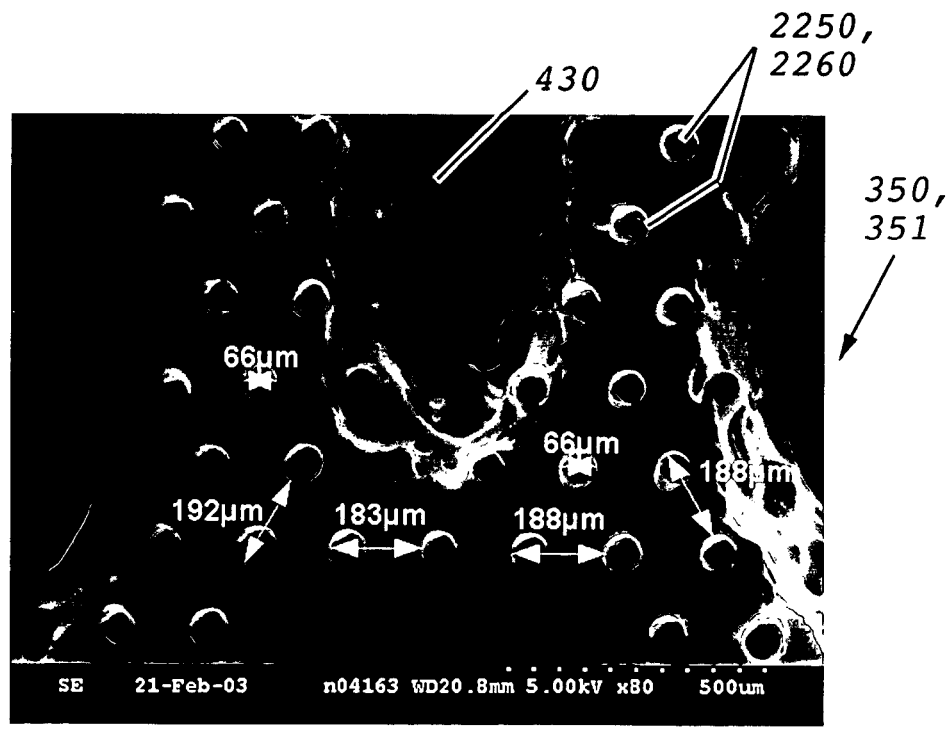
FIG. 25 is a photomicrograph showing a further enlarged portion of the forming structure shown in FIG. 24.

One two-stage method for making flexible polymeric forming structure 350, such as the forming structure shown in FIGS. 24-26, is described with reference to FIG. 23. The method described herein makes forming structures 350 having a combination of relatively large openings, i.e., depressions 710, and relatively fine protrusions, i.e., protrusions 2250. In the preferred embodiment illustrated in FIG. 23, the method described herein makes continuous belted forming structures 351. In broad outline, the method involves using a photosensitive resin to construct in and about a foraminous element a solid, polymeric framework which delineates the preselected patterns of the relatively large depressions 710 and relatively fine protrusions 2250 of forming structure 350 (or belted forming structure 351). More particularly, the method comprises a two stage resin casting process including the steps of:

a. Applying a backing film to the working surface of a forming unit;

b. Juxtaposing a foraminous element to the backing film so that the backing film is interposed between the foraminous element and the forming unit;

c. Applying a coating of liquid photosensitive resin to the surfaces of the foraminous element;

d. Controlling the thickness of the coating to a preselected value;

e. Juxtaposing in contacting relationship with the coating of photosensitive resin a mask comprising both opaque and transparent regions where the opaque regions define a preselected pattern corresponding to depressions 710;

f. Exposing the liquid photosensitive resin to light having an activating wavelength through the mask thereby inducing at least partial curing of the photosensitive resin in those regions which are in register with the transparent regions of the mask; and g. Removing from the composite foraminous element/partially cured resin substantially all the uncured liquid photosensitive resin;

h. Repeating one time steps a-g with a different controlled thickness (e.g., a greater thickness, such as a thickness corresponding to hf2 in FIG. 22) in step (d) and a different mask in step (e), the mask in step (e) comprising both opaque and transparent regions where the transparent regions define a preselected pattern corresponding to protrusions 2250;

i. Immersing the foraminous element/cured resin in an oxygen-free environment such as a water bath or other aqueous solution;

j. Exposing the foraminous element/partially cured resin to light having an activating wavelength through the mask thereby inducing full curing of the photosensitive resin, resulting in the finished belted forming structure.

The exact apparatus (or equipment) used in the practice of the present invention is immaterial so long as it can, in fact, be used to practice the present invention. After reading the whole of the following description, one of ordinary skill of the art will be able to select appropriate apparatus to perform the steps indicated above. A preferred embodiment of an apparatus which can be used in the practice of this invention to construct a forming structure in the form of an endless belt is shown in schematic outline in FIG. 23. For convenience, the invention will be described in terms of that apparatus.

The first step of the process is applying a backing film to the working surface of a forming unit. In FIG. 23, forming unit 613 has working surface 612 and is indicated as being a circular element; it is preferably a rotatable drum. The diameter of the forming unit 613 and its length are selected for convenience. Its diameter should be great enough so that the backing film and the foraminous element are not unduly curved during the process. It must also be large enough in diameter that there is sufficient distance of travel about its surface so that the necessary steps can be accomplished as the forming unit 613 is rotating. The length of the forming unit 613 is selected according to the width of the forming structure 350 being constructed. Forming unit 613 is rotated by a drive means not illustrated. Optionally, and preferably, working surface 612 absorbs light of the activating wavelength. Preferably, forming unit 613 is provided with means for insuring that backing film 653 is maintained in close contact with working surface 612. Backing film 653 can be, for example, adhesively secured to working surface 612 or forming unit 613 can be provided with means for securing backing film 653 to working surface 612 through the influence of a vacuum applied through a plurality of closely spaced, small orifices across working surface 612 of forming unit 613. Preferably, backing film 653 is held against working surface 612 by tensioning means not shown in FIG. 23.

Backing film 653 can be introduced into the system from backing film supply roll 631 by unwinding it therefrom and causing it to travel in the direction indicated by directional arrow D3. Backing film 653 contacts working surface 612 of forming unit 613, is temporarily constrained against working surface 612 by the means discussed hereinbefore, travels with forming unit 613 as the latter rotates, is eventually separated from working surface 612, and travels to backing film take-up roll 632 where it is rewound.

In the embodiment illustrated in FIG. 23, backing film 653 is designed for a single use after which it is discarded. In an alternate arrangement, backing film 653 can take the form of an endless belt traveling about a series of return rolls where it is cleaned as appropriate and reused. Necessary drive means, guide rolls, and the like are not illustrated in FIG. 23. The function of the backing film 653 is to protect the working surface 612 of the forming unit 613 and to facilitate removal of the partially cured forming structure 350 from the forming unit. The film can be any flexible, smooth, planar material such as polyethylene or polyester sheeting. Preferably, the backing film 653 is made from polypropylene and is from about 0.01 to about 0.1 millimeter (mm) thick.

The second step of the process is the juxtaposing of a foraminous element 601 to the backing film in such a way that the backing film is interposed between the foraminous element 601 and the forming unit 613. The foraminous element 601 is the material about which the curable resin is constructed. One suitable foraminous element is a metal wire screen 430 as illustrated in FIGS. 21 and 22. Screens having polyester filaments are suitable. Screens having mesh sizes from of about 6 to about 30 filaments per centimeter are suitable. Square weave screens are suitable as are screens of other, more complex weaves. Filaments having either round or oval cross sections are preferred. Although advantageous, it is not necessary that the filaments be transparent to light of the activating wave-length. In addition to screens, foraminous elements can be provided by woven and nonwoven fabrics, papermaking fabrics, thermoplastic netting, and the like. The precise nature of the foraminous element selected and its dimensions will be dictated by the use in which the forming structure 350 will be placed after it is constructed. Since the forming structure 350 constructed by the apparatus illustrated in FIG. 23 is in the form of an endless belt, foraminous element 601 is also an endless belt, formed, for example, by seaming together the ends of a length of screening.

As illustrated in FIG. 23, foraminous element 601 travels in the direction indicated by directional arrow D1 about return roll 611 up, over, and about forming unit 613 and about return rolls 614 and 615. Other guide rolls, return rolls, drive means, support rolls and the like can be utilized as necessary, and some are shown in FIG. 23. Foraminous element 601 is juxtaposed backing film 653 so that backing film 653 is interposed between foraminous element 601 and forming unit 613. The specific design desired for the forming structure 350 will dictate the exact method of juxtaposition. In the preferred embodiment, foraminous element 601 is placed in direct contacting relation with backing film 653.

When the liquid photosensitive resin 652 is applied to foraminous element 601 from source 620, the resin 652 will be disposed principally to one side of foraminous element 601 and foraminous element 601 will, in effect, be located at one surface of the forming structure 350. Foraminous element 601 can be spaced some finite distance from backing film 653 by any convenient means, but such arrangement is not usually preferred. Resin source 620 can be a nozzle, or any of known means for depositing liquid photosensitive resin, including extrusion, slot coating, and the like.

The third step in the process of this invention is the application of a first layer of coating of liquid photosensitive resin 652 to the foraminous element 601. The first layer of coating is the layer that will ultimately comprise the portion of forming structure 350 between the planes of the first and second surfaces, 1020 and 1060, respectively (shown as hf1 in FIG. 22). Any technique by which the liquid material can be applied to the foraminous element 601 is suitable. For example, nozzle 620 can be used to supply viscous liquid resin. It is necessary that liquid photosensitive resin 652 be evenly applied across the width of foraminous element 601 prior to curing and that the requisite quantity of material be applied so as to enter the openings of the foraminous member 601 as the design of the forming structure 350 requires. For woven foraminous elements the knuckles, i.e., the raised cross-over points of a woven screen structure, are preferably in contact with the backing film, so that it will likely not be possible to completely encase the whole of each filament with photosensitive resin; but as much of each filament as possible should be encased.

Suitable photosensitive resins can be readily selected from the many available commercially. They are materials, usually polymers, which cure or cross-link under the influence of radiation, usually ultraviolet (UV) light. References containing more information about liquid photo-sensitive resins include Green et al, "Photocross-linkable Resin Systems", J. Macro-Sci. Revs. Macro Chem., C21 (2),187-273 (1981-82); Bayer, "A Review of Ultraviolet Curing Technology", Tappi Paper Synthetics Conf. Proc., Sept. 25-27, 1978, pp. 167-172; and Schmidle, "Ultraviolet Curable Flexible Coatings", J. of Coated Fabrics, 8, 10-20 (July, 1978). All the preceding three references are incorporated herein by reference. Especially preferred liquid photosensitive resins are included in the Merigraph L-055 series of resins made by MacDermid Imaging Technology Inc., Wilmingtion, Del., USA USA.

The next step in the process of this invention is controlling the thickness of the coating to a preselected value. The preselected value corresponds to the thickness desired for the forming structure 350 between first and second surfaces 1020 and 1060, respectively. That is, the thickness $hf_1$ as shown in FIG. 22. When the forming structure 350 is to be used to make the web 80 suitable for use as a topsheet in a disposable absorbent article, it is preferred that hf1 be from about 1 mm to about 2 mm thick. Other applications, of course, can require thicker forming structures 350 which can be 3 mm thick or thicker.

Any suitable means for controlling the thickness can be used. Illustrated in FIG. 23 is the use of nip roll 641. The clearance between nip roll 641 and forming unit 613 can be controlled mechanically by means not shown. The nip, in conjunction with mask 654 and mask guide roll 641, tends to smooth the surface of liquid photosensitive resin 652 and to control its thickness.

Figure 27:
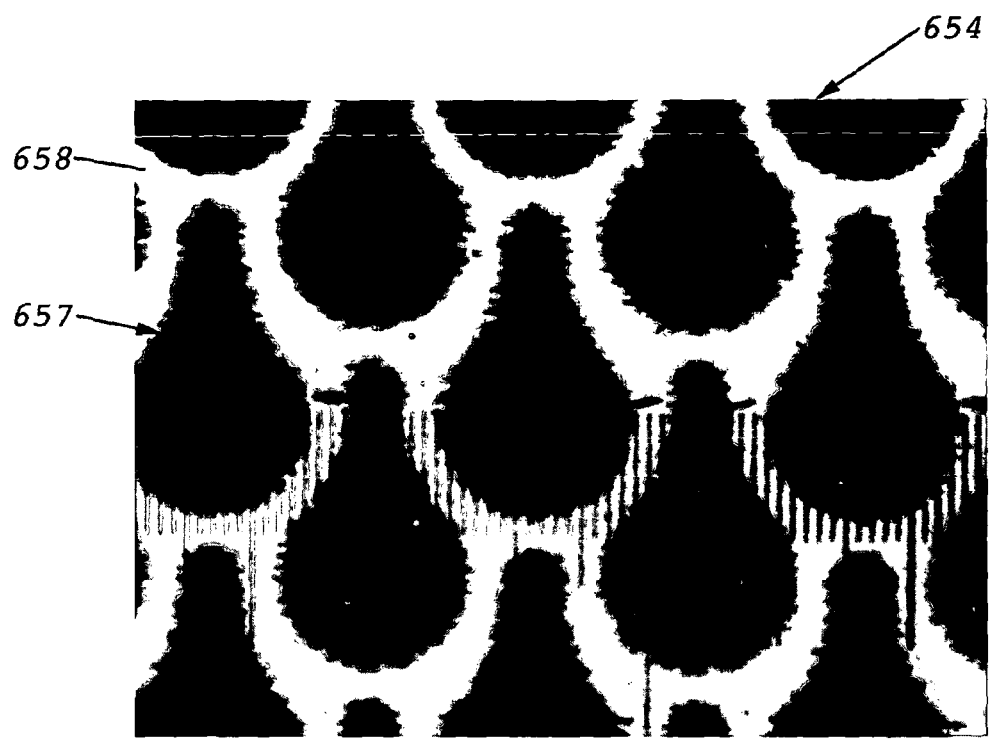
FIG. 27 is a representation of a first mask used in a process for making a forming structure of the present invention.

The fifth step in the process of the invention comprises juxtaposing a first mask 654 in contacting relation with the liquid photosensitive resin 652. The purpose of the mask is to shield certain areas of the liquid photosensitive resin from exposure to light. First mask 654 is transparent to activating wavelengths of light, e.g., UV light, except for a pattern of opaque regions corresponding to the pattern of apertures 71 desired in the forming structure 350. A portion of a suitable first mask 654 showing one pattern of opaque, i.e., shaded, portions 657 and light-transparent portions 658 is shown in FIG. 27. Note that FIG. 27 shows a measuring scale superimposed thereunder. The smallest increment of the scale shown is 0.1 mm.

The light-transparent portions 658 of first mask 654, i.e., the areas that are not shielded from the activating light source correspond to those areas of liquid photosensitive resin that will be cured to form the connecting members 910 of forming structure 350. Likewise, the opaque portions 657 of first mask 654 correspond to pattern of the depressions 710 of forming structure 350. First mask 654, can, therefore, have opaque portions 657 corresponding to the pattern of hexagon-shaped depressions of forming structure 350 shown in FIG. 21, or the pentagonal-shaped depressions 710 shown in FIG. 13, or the teardrop-shaped depressions 710 shown in FIG. 15. In general, for a forming structure 350 used to form a web 80 for use as a topsheet in a disposable absorbent article, the opaque portions 657 of first mask 654 should be of a suitable size, shape, and spacing to provide the necessary structure of apertures 71 for web 80 such that it exhibits desirable fluid flow properties.

First mask 654 can be any suitable material which can be provided with opaque and transparent regions. A material in the nature of a flexible film is suitable. The flexible film can be polyester, polyethylene, or cellulosic or any other suitable material. The opaque regions can be formed by any convenient means such as photographic or gravure processes, flexographic processes, and inkjet or rotary screen printing processes. First mask 654 can be an endless loop or belt (the details of which are not shown) or it can be supplied from one supply roll and transverse the system to a takeup roll, neither of which is shown in the illustration. First mask 654 travels in the direction indicated by directional arrow D4, turns under nip roll 641 where it is brought into contact with the surface of liquid photosensitive resin 652, travels to mask guide roll 642 in the vicinity of which it is removed from contact with the resin. In this particular embodiment, the control of the thickness of the resin and the juxtaposition of the mask occur simultaneously.

The sixth step of the process of this invention comprises exposing the liquid photosensitive resin 652 to light of an activating wavelength through the first mask 654 thereby inducing at least partial curing of the resin in those regions which are in register with the transparent regions 658 of first mask 654. The resin need not be fully cured in this step, but at least partial curing is achieved when exposed resin retains its desired shape during post-light-exposure steps, such as washing away non-cured resin, as described below. In the embodiment illustrated in FIG. 23, backing film 653, foraminous element 601, liquid photosensitive resin 652, and mask 654 all form a unit traveling together from nip roll 641 to the vicinity of mask guide roll 642. Intermediate nip roll 641 and mask guide roll 642 and positioned at a location where backing film 653 and foraminous element 601 are still juxtaposed forming unit 613, liquid photosensitive resin 652 is exposed to light of an activating wavelength as supplied by exposure lamp 655. Exposure lamp 655 is selected to provide illumination primarily within the wavelength which causes curing of the liquid photosensitive resin. That wavelength is a characteristic of the liquid photosensitive resin. In a preferred embodiment the resin is UV-light curable and exposure lamp 655 is a UV light source. Any suitable source of illumination, such as mercury arc, pulsed xenon, electrodeless, and fluorescent lamps, can be used.

As described above, when the liquid photosensitive resin is exposed to light of the appropriate wavelength, curing is induced in the exposed portions of the resin. Curing is generally manifested by a solidification of the resin in the exposed areas. Conversely, the unexposed regions remain fluid. The intensity of the illumination and its duration depend upon the degree of curing required in the exposed areas. The absolute values of the exposure intensity and time depend upon the chemical nature of the resin, its photo characteristics, the thickness of the resin coating, and the pattern selected. Further, the intensity of the exposure and the angle of incidence of the light can have an important effect on the presence or absence of taper in the walls of connecting members 910 through the thickness hf1 of forming structure 350. Accordingly, the light can be collimated to achieve the desired degree of taper.

The seventh step in the process is removing from the cured or partially-cured composite of foraminous element/partly cured resin 621 substantially all of the uncured liquid photosensitive resin. That is to say, the resin which has been shielded from exposure to light is removed from the system. In the embodiment shown in FIG. 23, at a point in the vicinity of mask guide roll 642, first mask 654 and backing film 653 are physically separated from the composite comprising foraminous element 601 and the now partly cured resin 621. The composite of foraminous element 601 and partly cured resin 621 travels to the vicinity of first resin removal shoe 623. A vacuum is applied to one surface of the composite at first resin removal shoe 623 so that a substantial quantity of the liquid (uncured) photosensitive resin is removed from the composite. As the composite travels farther, it is brought into the vicinity of resin wash shower 624 and resin wash station drain 625 at which point the composite is thoroughly washed with water or other suitable liquid to remove more of the remaining liquid (uncured) photosensitive resin, which is discharged from the system through resin wash station drain 625. The wash shower is preferably primarily water or an aqueous solution at a temperature above about 115 degrees F.

A second resin removal shoe 626 (or a third, etc., as necessary) can be used for further removal of residual un-cured resin at this stage of the process. (A second curing station in the form of a second light source 660 and an air-displacing medium, such as water bath 630, is shown in FIG. 23 but is not used in the first stage of the process.)

At this stage of the process for making forming structure 350, which is the end of the first stage, the composite now comprises essentially foraminous element 601 and the partially-cured resin 621 that represents the portion of forming structure 350 comprising connecting elements 910, first surface 900 and second surface 850 and depressions 710.

The next step is to form protrusions 2250 on the partially-formed forming structure 350. To form protrusions 2250, the process is essentially repeated in a second stage, and with a second mask 656 replacing first mask 654.

Therefore, step eight starts with partially formed forming structure, denoted as 603 in FIG. 23 advancing in the direction indicated by directional arrow D1 about return roll 611 up, over, and about forming unit 613 and about return rolls 614 and 615. As before, other guide rolls, return rolls, drive means, support rolls and the like can be utilized as necessary, and some are shown in FIG. 23. Partially formed forming structure 603 is juxtaposed backing film 653 so that backing film 653 is interposed between partially formed forming structure 603 and forming unit 613. The specific design desired for the forming structure 350 will dictate the exact method of juxtaposition. In the preferred embodiment, partially formed forming structure 603 is placed in direct contacting relation with backing film 653. Backing film 653 can be the same backing film referred to previously for the first stage of the process.

In the ninth step of the process a second coating of liquid photosensitive resin 652 is again applied as discussed above to partially formed forming structure 603 from source 620, the resin 652 being applied to fill the depressions, i.e., depressions 710, of partially formed forming structure 603 and, in addition, apply a coating above the level of partially cured resin of partially formed forming structure 603. As before, partially formed forming structure 603 can be spaced some finite distance from backing film 653 by any convenient means, but such arrangement is not usually preferred.

The second layer of coating is the layer will ultimately be cured to form the protrusions 2250 of forming structure 350. If uniform heights of protrusions 2250 are desired, it is necessary that the second layer of liquid photosensitive resin 652 be evenly applied across the width of partially formed forming structure 603. A requisite quantity of photosensitive resin to form protrusions 2250 is enough so as to fill the openings of the partially formed forming structure 603 and to over fill to a preselected thickness corresponding to the desired protrusion height, such as a thickness corresponding to distance hf2 of FIG. 22. When the forming structure 350 is to be used to make the web 80 suitable for use as a topsheet in a disposable absorbent article, it is preferred that hf2 be from about 1.1 mm to about 2.1 mm thick. As before, any suitable means for controlling the thickness can be used, including the use of nip roll 641.

Figure 28:
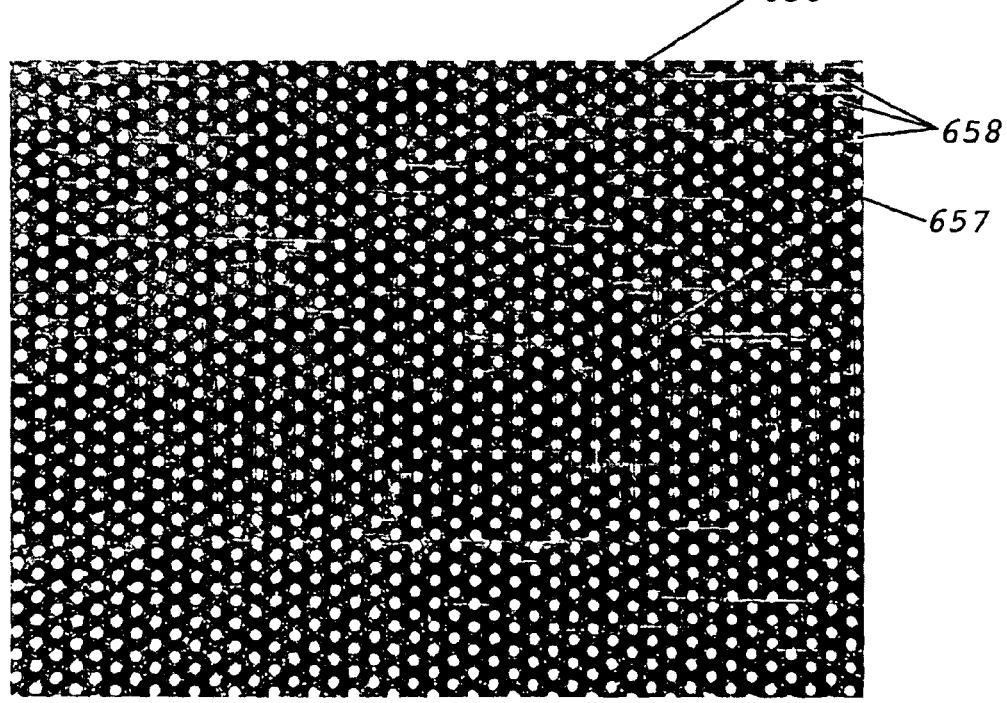
FIG. 28 is a representation of a second mask used in a process for making a forming structure of the present invention.

The tenth step in the process illustrated in FIG. 23 comprises juxtaposing a second mask 656 in contacting relation with the second layer of liquid photosensitive resin 652. As before, the purpose of the mask is to shield certain areas of the liquid photosensitive resin from exposure to light. A portion of a suitable first mask 654 showing one pattern of opaque, i.e., shaded, portions 657 and light-transparent portions 658 is shown in FIG. 28. Note that, although difficult to see, FIG. 28 shows a measuring scale superimposed thereunder. The smallest increment of the scale shown is 0.1 mm.

As shown in FIG. 28, second mask 656 is opaque to activating wavelengths of light, e.g., UV light, except for a pattern of transparent regions 658 corresponding to the pattern of protrusions 2250 desired in the forming structure 350. The light-transparent portions of second mask 656, i.e., the areas that are not shielded from the activating light source correspond to those areas of liquid photosensitive resin that will be cured. Therefore, the transparent regions of second mask 656 correspond to the preselected pattern of the protrusions 2250 of forming structure 350. Second mask 656, can, therefore, have a pattern of transparent regions being closely-spaced spots or dots, which spots or dots have a one-to-one correspondence to the closely-spaced, round (in cross-section) protrusions, such as those shown in FIGS. 24 and 25. The pattern of transparent regions of mask 656 can, of course, be other shapes and patterns, depending on the particular end use of forming structure 350. In general, for a forming structure 350 used to form a web 80 for use as a topsheet in a disposable absorbent article, the transparent regions 658 of second mask 656 should be of a suitable size, shape, and spacing to provide the necessary structure of protrusions 2250 for web 80 such that it exhibits desirable tactile properties, such as perceived softness. In one embodiment, transparent regions 658 of second mask 656 are each circular with a diameter of about 65 microns, spaced apart on a center-to-center distance of about 188 microns, in a uniform spacing of about 3875 transparent regions 658 per square centimeter (about 25,000 per square inch).

Second mask 656 can be the same material as first mask 654 such as a flexible film in which the opaque regions can be applied by any convenient means such as photographic or gravure processes, flexographic processes, and inkjet or rotary screen printing processes. Second mask 656 can be an endless loop (the details of which are not shown) or it can be supplied from one supply roll and transverse the system to a takeup roll, neither of which is shown in the illustration. Second mask 656 travels in the direction indicated by directional arrow D4, turns under nip roll 641 where it is brought into contact with the surface of liquid photosensitive resin 652, travels to mask guide roll 642 in the vicinity of which it is removed from contact with the resin. In this particular embodiment, the control of the thickness of the resin and the juxtaposition of the mask occur simultaneously.

The eleventh step of the process comprises again exposing the liquid photosensitive resin 652 to light of an activating wavelength through the second mask 656 thereby inducing curing of the resin in those regions which are in register with the transparent regions of second mask 656, that is, protrusions 2250. In the embodiment illustrated in FIG. 23, backing film 653, partially formed forming structure 603, liquid photosensitive resin 652, and second mask 656 all form a unit traveling together from nip roll 641 to the vicinity of mask guide roll 642. Intermediate nip roll 641 and mask guide roll 642 and positioned at a location where backing film 653 and partially formed forming structure 603 are still juxtaposed forming unit 613, liquid photosensitive resin 652 is exposed to light of an activating wavelength as supplied by exposure lamp 655. As before, exposure lamp 655, in general, is selected to provide illumination primarily within the wavelength which causes curing of the liquid photosensitive resin. That wavelength is a characteristic of the liquid photosensitive resin. As before, n a preferred embodiment the resin is UV-light curable and exposure lamp 655 is a UV light source (in fact, is the same light source used in the first stage of the process, described above).

As described above, when the liquid photosensitive resin is exposed to light of the appropriate wavelength, curing is induced in the exposed portions of the resin. Curing is manifested by a solidification of the resin in the exposed areas. Conversely, the unexposed regions remain fluid (or partially-cured in the case of the previously-cured portions of partially formed forming structure 603). The intensity of the illumination and its duration depend upon the degree of curing required in the exposed areas. The absolute values of the exposure intensity and time depend upon the chemical nature of the resin, its photo characteristics, the thickness of the resin coating, and the pattern selected. Further, the intensity of the exposure and the angle of incidence of the light can have an important effect on the presence or absence of taper in the walls of the protrusions 2250. As mentioned before, a light collimator can be utilized to reduce tapering of the walls.

The twelfth step in the process is again removing from the partially-cured forming structure 350 substantially all of the uncured liquid photosensitive resin. That is to say, the resin which has been shielded from exposure to light in the second curing step is removed from the system. In the embodiment shown in FIG. 23, at a point in the vicinity of mask guide roll 642, second mask 656 and backing film 653 are physically separated from the now partly cured resin 621 which now includes partially- or substantially fully-cured resin of the completed forming structure 350, i.e., having both depressions 710 and protrusions 2250. The partly cured resin 621 travels to the vicinity of first resin removal shoe 623. A vacuum is applied to one surface of the composite at first resin removal shoe 623 so that a substantial quantity of the liquid (uncured) photosensitive resin, as well as cured "protrusions" adjacent depressions 710, is removed from the composite. Note that in the second curing step, second mask 656 does not limit curing of resin only on portions corresponding to first surface 900 of forming structure 350. The second curing step actually cures "protrusions" uniformly across the entire area of partially cured composite 603. However, only portions of cured resin over connecting members 910 join to connecting members 910 at first surface 900 and become essentially integral with the previously-cured resin portions. Thus, in the vacuum and water washing steps, the portions of cured resin corresponding to "protrusions" that are in the adjacent depressions 710 are simply removed to prior to a final light-exposure for final curing, as described more fully below.

As the composite travels farther, it is brought into the vicinity of resin wash shower 624 and resin wash station drain 625 at which point the composite is thoroughly washed with water or other suitable liquid to remove substantially all of the remaining liquid (uncured) photosensitive resin, as well as any cured resin not forming part of the finished forming structure 350, all of which is discharged from the system through resin wash station drain 625 for recycling or disposal. For example, cured resin formed in the second stage light activation in the regions of the depressions are washed away. Such cured resin is preferably non-adhered to the underlying foraminous member, and, if adhered, the level of adhesion is preferably insufficient to prevent the unwanted cured material to wash away.

After substantially all of the uncured resin is removed and the remaining resin is in the final form for forming structure 350, the remaining resin is fully cured by a second light source 660, preferably in an oxygen free medium, such as water bath 630. The oxygen free medium ensures that oxygen does not interfere with the final UV-light curing of the remaining uncured resin. Oxygen can slow down or stop chain growth in free radical polymerization.

As shown in FIG. 23 a series of guide roll 616 can be used as required to guide the partially-formed forming structure 350 into a water bath 630. However, in practice, any process configuration can be used, including simply letting the partially-formed forming structure 350 be immersed in shallow, e.g., 25.4 mm deep, water tray by its own weight. The final exposure of the resin to activating light 660 ensures complete curing of the resin to its fully hardened and durable condition.

The above-described twelve-step, two-stage process continues until such time as the entire length of foraminous element 601 has been treated and converted into the forming structure 350. The finished forming structure, denoted as belted forming structure 351, can then be used in a web forming process, such as the process described with reference to FIG. 29, for example.

Therefore, in general, curing can be done in stages, so that first a negative mask having UV blocking portions corresponding to forming structure apertures 710 (having UV blocking portions in a pattern of teardrops, for example), can be used to first partially cure the polymer by directing a UV light source orthogonal to the mask for a sufficient amount of time. Once the polymer is partially cured in the unmasked areas, a second mask comprising a plurality of closely spaced UV-transparent spots or dots can be placed between the light source and the partially cured polymer. The polymer is again cured by UV-light to fully cure the portions of the polymer that will be the protrusions 2250. Once the protrusions are fully cured, the remaining uncured polymer (and partially cured polymer) can be removed to leave a forming structure having similar characteristics as those shown in FIGS. 22-26. The procedure described can be used for prototyping hand sheets of material, for example.

Example of Formation of Belted Forming Structure:

The forming structure 350 shown in FIGS. 24-26 was made according to the process described above with respect to FIG. 23. In particular, foraminous element 601 was an 18×16 mesh bright aluminum screening available from Hanover Wire Cloth Star Brand Screening, Hanover, Pa. The screening was approximately 0.5 mm (0.021 inches) thick, 61 cm (24 inches) wide and comprised a woven mesh of filaments, each filament having filament diameter of about 0.24 mm. The screening was about 15 meters (50 feet) long and was formed into an endless belt by a sewn seam.

The backing film was a 0.1 mm (0.004 inch) thick biaxially clear polyester film, available as Item No. R04DC30600 from Graphix, 19499 Miles Road, Cleveland, Ohio, USA. The photosensitive resin was XPG2003-1 purchased from MacDermid Imaging Technology Inc., Wilmingtion, Del., USA USA which was used at room temperature as received from the manufacturer.

The first mask was a 0.1 mm (0.004 inch) Color Clear Film, 787N, available from Azon of Chicago Ill., USA and was printed with teardrop pattern as shown in FIG. 27. The first mask was created by inkjet printing the pattern directly onto the Azon Color Clear Film.

The forming unit comprised a drum about 108 cm (42.5 inches) in diameter and about 71 cm (28 inches) wide. It rotated with a surface velocity of about 41 cm (16 inches) per minute.

For the first cast, the photosensitive resin was applied through a nozzle to a controlled overall thickness of about 1.7 mm (0.067 inches), with the thickness being controlled by the spacing of the forming unit and nip roll as described above.

The exposure lamp, i.e., lamp 655 discussed above, was a UV light system VPS/1600 system, Model No. VPS-6, purchased from Fusion UV Systems, 910 Clopper Road, Gaithersburg, Md., USA. The exposure lamp was placed about 35 cm (14 inches) from the first mask and the exposure was controlled by a quartz aperture (optional, a quartz aperture helps create a uniform light density across the exposed area of the mask) which was positioned about 6.4 mm (2.5 inches) from the surface of the mask, and which extended the width of the forming unit and about 10 cm (4 inches) in the direction of travel (i.e., about the periphery of forming drum 613). The light was collimated (collimator is optional but helps collimate the light for better curing resolution) through a 12.5 mm (0.5 inch) hexagonal honeycomb collimator that was 38 mm (1.5 inches) tall (i.e., 38 mm long tubes having a honeycomb structure).

After the first resin layer was exposed to UV light, the first mask was separated from the composite of partially-cured resin and the uncured resin was washed from the composite by an aqueous solution of water (100 gallons/per minute), Mr. Clean® (0.065 gallons/minute) and Merigraph System W6200 defoamer (0.089 gallons/minute) at a temperature of about 115 degrees F. through 4 sets of showers, each comprising a 28 inch wide manifold of 17 nozzles. Three showers sprayed from the top of the composite and one from the bottom.

After the first stage the composite was partially cured, which means that the first cast of resin was not fully cured by second UV source, e.g., lamp 660 described above. The partially cured composite comprising the first cast of resin now comprised the teardrop shaped depressions 710 of forming structure 350. The first cast of resin exhibited a thickness above the foraminous element of about 1.3 mm (0.050 inch). The partially cured composite was run back over the forming unit a second time in the second stage of the process. The same photosensitive resin was applied to an overall thickness of about 2 mm (0.077 inches), which was about 0.24 mm (0.010 inches) thicker than the first application of resin. A second mask was used, the second mask having a pattern of small transparent circles 0.08 mm (0.003 inches) in diameter and spaced 0.18 mm (0.007 inches) center-to-center in an equilateral triangle array as illustrated in FIG. 28.

The composite was cured again by light source 655 as described above and subjected to the showers 624, as described above. After the showers removed substantially all of the uncured resin, the composite was post cured by directing a post-cure UV light at the composite, e.g., from source 660, while the composite was submerged in 2.5 cm (1 inch) of water containing 36 grams of sodium sulfite/gallon of water.

The sodium sulfite is optional, but is a good oxygen scavenger. The post-cure UV light source was placed about 20 cm (8 inches) from the composite.

The resulting belted forming structure 351 exhibited columnar-shaped pillars (i.e., protrusions 2250) having a substantially uniform circular cross-section extending from the first surface. The protrusions each had a height about 105 microns, a diameter of about 66 microns, and a center-to-center spacing of about 188 microns. The belted forming structure 351 additionally exhibited uniform teardrop-shaped depressions 710. Photomicrographs of representative portions of the belted forming structure made by the process described above are shown in FIGS. 24-26. Note that protrusions are seamless, integral extensions of the first surface of the forming structure. This is believed to be due to the polymer being only partially cured in the first stage of the process, and finally cured after formation of the protrusions.

Other methods of making forming structures are contemplated, including creation via a molding technique, in which the forming structure 350 is cast in a negative impression mold, cured, and removed. In one embodiment, a substrate, such as a polymeric substrate can be laser machined to form the negative of forming structure 350, i.e., a mold having the internal shape of forming structure 350. Once laser machined, a polymer could be directly cast into the mold (with appropriately-applied release agents, and the like, as is known in the art). The resulting forming structure 350 would have the positive shape of the mold. Alternatively, the laser-machined mold could have built up therein by electroplating, for example, a metallic forming structure 350. Also, forming structures could be formed by way of electroplating techniques, in which successive layers of material are built up into a suitable form.

One of the advantages to making forming structure 350 from a flexible polymeric material, such as the material described with respect to FIGS. 15 and 24-26 is that the forming structure is flexible enough to be utilized as a continuous belt, much like a papermaking belt is used in the above-mentioned Trokhan '289 patent. Such a continuous belt is referred to herein as a flexible "belted" forming structure 351. By "belted" is meant that the forming structure is in the form of a continuous, flexible band of material, much like a conveyor belt, as opposed to a relatively rigid tubular drum-shaped structure.

Figure 29:
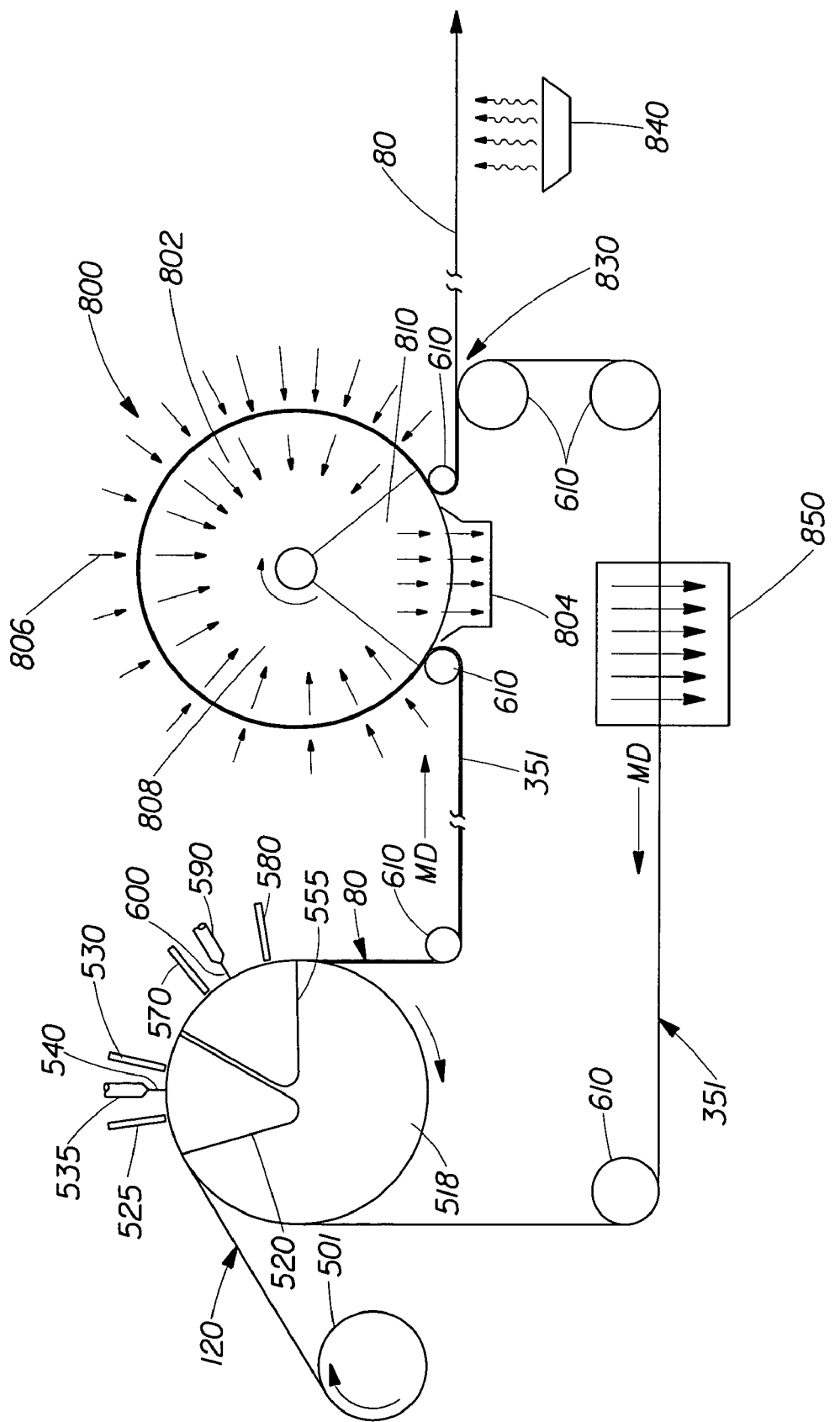
FIG. 29 is a simplified schematic illustration of a process for making a web using a belted forming structure of the present invention.

FIG. 29 shows in simplified schematic representation one embodiment of a process for making a polymeric web 80 of the invention using a flexible belted forming structure 351. As shown, belted forming structure 351 can be a continuous belted member guided and held tensioned by various rollers, e.g., rollers 610. Belted forming structure 351 is guided over forming drum 518. While on forming drum 518 belted forming structure is supported by forming drum 518 and precursor film 120 is supported on forming structure 351. The formation of web 80 on forming structure 351 proceeds the same way as described above with respect to FIG. 9 and forming drum 350. Therefore, precursor web 120 can be subjected to liquid jet 540, (or jets) as well as drying means 590 (or drying/annealing means). However, in the process described schematically in FIG. 29, drying means 590 on forming drum 518 is optional, because drying (and/or annealing) is provided for elsewhere in the process, as described more fully below. Therefore, in the embodiment described with respect to FIG. 29, drying means 590 can be replaced by re-heat means to further form precursor web 120.

In one embodiment, liquid jets 540 are not used, and the process is essentially a liquid-free process. In such a process liquid jets 540 and or drying means 590 are replaced by re-heat means as described above. Precursor film 120 is heated by reheat means that, together with vacuum if necessary, conform precursor web 120 to forming structure 351. Because no liquid is used in this process, no drying is necessary, and the drying steps disclosed herein can be eliminated.

As can be seen in FIG. 29, belted forming structure 351 does not simply rotate on forming drum 518 but is guided onto and off of forming drum 518. As belted forming structure 351 is guided onto forming drum 518 it is preferably dry. After belted forming structure 351 is supported by forming drum 518, or concurrently therewith, precursor web 120 is guided over belted forming structure 351 and hydroformed as described above. After passing drying means 590 the belted forming structure 351 and a three-dimensional, apertured, formed film web 80 of the present invention are guided off of forming drum 518 together. That is, polymer web 80 is intimately in contact with and supported by belted forming structure 351. This permits further processing, such as drying or annealing, if necessary, to take place while the polymer web 80 is still supported by the belted forming structure 351. In this manner, polymer web 80 can endure much greater work without collapsing, tearing, or otherwise deforming in a negative manner.

Belted forming structure 351 and polymer web 80 are guided in the direction indicated in FIG. 29, i.e., the machine direction, to a through-air drying means 800. Through air drying means can be in the form of a rotating drum as shown in FIG. 29, but can be in any of other known configurations. Drying means 800 preferably utilizes air which is forced through polymer web 80 and belted forming structure 351 to effect drying of the web. However, other drying means are contemplated, such as the use of capillary drying or limited orifice drying techniques common in the papermaking industry for drying paper webs.

Drying means shown in FIG. 29 comprises rotating porous drying drum 802. As belted forming structure 351 and polymeric web 80 are supported by drying drum 802 a drying fluid, such as air, is forced through belted forming structure 351 and polymeric web 80. Fluid, such as air, can be forced from the outside to the inside of drying drum 802, as shown in FIG. 29, or it can be forced from the inside to the outside. In either configuration, the point is that the fluid effects drying of polymeric web 80 while web 80 remains fully supported on belted forming structure 351. Drying drum dimensions, fluid flow rates, fluid moisture content, drying drum rotation velocity can all be adjusted as necessary to ensure adequate drying of polymeric web 80 prior to being guided off of drying drum 802.

Drying drum 802 can have a vacuum chamber 808 to aid in fluid flow through polymeric web 80 and belted forming structure 351. Additionally, fluid removal means can be utilized to remove liquid removed from polymeric web 80. Fluid removal means can include a simple drain in forming drum 802, but can also include active removal via pumps as is known in the art to recycle water back to the hydroforming apparatus. Drying drum 802 can have a positive pressure chamber 810 which aids in removing excess moisture from the surface of forming drum 802 prior to repeating the process of supporting belted forming structure 351. Liquid removed can be simply captured in container 804 and removed appropriately, such as by draining into a water recycle system.

Once polymeric web 80 and belted forming structure 351 are guided off of drying drum 802, polymeric web 80 is separated from belted forming structure 351 at separation point 830. From this point polymeric web 80 may be, if necessary, subjected to additional drying, such as by radiant heat drying means 840, and likewise, belted forming structure may be subjected to additional drying means, such as forced air drying means 850. In all cases, other drying means as suitable under the processing conditions can be utilized as necessary to ensure that polymeric web 80 is sufficiently dry prior to final processing into roll stock and belted forming structure 351 is sufficiently dry to avoid introducing moisture into the interior of hair like fibrils 225 of polymeric web 80. Sufficiently dry means dry enough such that post-manufacture moisture related problems such as mold or mildew in the polymeric web are minimized or eliminated.

What is claimed is:

1. A method for making a forming structure, the method comprising the steps of:
    a) providing a base material consisting essentially of a polymeric material and having a thickness;
    b) providing a laser source;
    c) laser etching a plurality of spaced-apart apertures, each aperture extending through the entire thickness of the base material, such that the non-laser-etched portions of the base material define a continuous network; and
    d) laser etching the continuous network to remove material in a pattern that defines a plurality of protrusions, each protrusion being generally columnar and pillar-like and having an aspect ratio of at least 1, wherein said protrusions have a center-to-center spacing between two adjacent protrusions between about 100 µm to about 250 µm.

2. The method of claim 1, wherein the polymeric material is chosen from the group consisting of polypropylene, acetal resin, PEEK, polyester, and epoxies.

3. The method of claim 1, wherein the base material is cylindrical shaped having a central longitudinal axis such that the forming structure is a rotatable drum.

4. The method of claim 1, wherein the protrusions have an average height of at least 50 microns.

5. The method of claim 1, wherein the protrusions have an average height of at least 75 microns and an average aspect ratio of at least 1.5.

6. The method of claim 1, wherein the protrusions have an average height of at least 100 microns and an average aspect ratio of at least 1.5.

7. The method of claim 1, wherein the protrusions have an average height of at least 150 microns and an average aspect ratio of at least 2.

8. The method of claim 1, wherein the protrusions have a height of at least 50 microns.

9. The method of claim 1, wherein said forming structure has a forming structure first surface, wherein the protrusions have a height of at least 75 microns and an aspect ratio of at least 1.5 and the forming structure first surface defines a first surface area and the forming structure comprises at least about 2325 protrusions per square centimeter of first surface area.

10. The method of claim 1, wherein the base material is a polymer comprising a particulate or fiber filler.

11. The method of claim 1, wherein the base material has a modulus of at least about 5 MPa and a strain at break of at least about 1%, each tested at a strain rate of 100% per minute.

12. The method of claim 1, wherein the base material has a modulus of at least about 200 MPa and a strain at break of at least about 5%, each tested at a strain rate of 100% per minute.

13. The method of claim 1, wherein the base material has a modulus of at least about 400 MPa and a strain at break of at least about 10%, each tested at a strain rate of 100% per minute.

14. The method of claim 1, wherein said forming structure has a forming structure first surface and the forming structure first surface defines a first surface area, wherein the plurality of protrusions comprises at least about 1550 protrusions per square centimeter of first surface area.

15. The method of claim 1, wherein said forming structure has a forming structure first surface and the forming structure first surface defines a first surface area, wherein the plurality of protrusions comprises at least about 2325 protrusions per square centimeter of first surface area.

16. The method of claim 1, wherein said forming structure has a forming structure first surface and the forming structure first surface defines a first surface area, wherein the plurality of protrusions comprises at least about 3100 protrusions per square centimeter of first surface area.

17. The method of claim 1, wherein said forming structure has a forming structure first surface and the forming structure first surface defines a first surface area, wherein the plurality of protrusions comprises at least about 3875 protrusions per square centimeter of first surface area.

18. A method for making a forming structure, the method comprising the steps of:
    a) providing a base material consisting essentially of a polymeric material and having a thickness;
    b) providing a laser source;
    c) laser etching the base material such that the non-laser-etched portions define a plurality of protrusions, each protrusion being generally columnar and pillar-like and having an aspect ratio of at least 1, wherein said protrusions have a center-to-center spacing between two adjacent protrusions between about 100 µm to about 250 µm; and
    d) laser etching a pattern that defines a plurality of spaced-apart apertures, each aperture extending through the thickness of the base material.

19. The method of claim 18, wherein the polymeric material is chosen from the group consisting of polypropylene, acetal resin, PEEK, polyester, and epoxies.

20. The method of claim 18, wherein the base material is cylindrical shaped having a central longitudinal axis such that the forming structure is a rotatable drum.

21. The method of claim 18, wherein the protrusions have an average height of at least 50 microns and an average aspect ratio of at least 1.

22. The method of claim 18, wherein the protrusions have an average height of at least 75 microns and an average aspect ratio of at least 1.5.

23. The method of claim 18, wherein the protrusions have an average height of at least 100 microns and an average aspect ratio of at least 1.5.

24. The method of claim 18, wherein the protrusions have an average height of at least 150 microns and an average aspect ratio of at least 2.

25. The method of claim 18, wherein the protrusions have a height of at least 50 microns.

26. The method of claim 18, wherein said forming structure has a forming structure first surface, wherein the protrusions have a height of at least 75 microns and an aspect ratio of at least 1.5 and the forming structure first surface defines a first surface area and the forming structure comprises at least about 2325 protrusions per square centimeter of first surface area.

27. The method of claim 18, wherein the base material is a polymer comprising a particulate or fiber filler.

28. The method of claim 18, wherein the base material has a modulus of at least about 5 MPa and a strain at break of at least about 1%, each tested at a strain rate of 100% per minute.

29. The method of claim 18, wherein the base material has a modulus of at least about 200 MPa and a strain at break of at least about 5%, each tested at a strain rate of 100% per minute.

30. The method of claim 18, wherein the base material has a modulus of at least about 400 MPa and a strain at break of at least about 10%, each tested at a strain rate of 100% per minute.

31. The method of claim 18, wherein said forming structure has a forming structure first surface and the forming structure first surface defines a first surface area, wherein the plurality of protrusions comprises at least about 1550 protrusions per square centimeter of first surface area.

32. The method of claim 18, wherein said forming structure has a forming structure first surface and the forming structure first surface defines a first surface area, wherein the plurality of protrusions comprises at least about 2325 protrusions per square centimeter of first surface area.

33. The method of claim 18, wherein said forming structure has a forming structure first surface and the forming structure first surface defines a first surface area, wherein the plurality of protrusions comprises at least about 3100 protrusions per square centimeter of first surface area.

34. The method of claim 18, wherein said forming structure has a forming structure first surface and the forming structure first surface defines a first surface area, wherein the plurality of protrusions comprises at least about 3875 protrusions per square centimeter of first surface area.

* * * * *